US007869983B2

(12) United States Patent  
Raby et al.

(10) Patent No.: US 7,869,983 B2
(45) Date of Patent: Jan. 11, 2011

(54) COMPUTING FINAL OCCLUSION WITH RESPECT TO TORQUE LOSS IN A THREE-DIMENSIONAL VIRTUAL ORTHODONTIC SYSTEM

(75) Inventors: Richard E. Raby, North St. Paul, MN (US); Nicholas A. Stark, Cottage Grove, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 1200 days.

(21) Appl. No.: 10/990,925

(22) Filed: Nov. 17, 2004

(65) Prior Publication Data

US 2006/0105286 A1 May 18, 2006

(51) Int. Cl.
G06F 7/60 (2006.01)
A61C 3/00 (2006.01)
(52) U.S. Cl. ............................................. 703/2; 433/24
(58) Field of Classification Search ................. 703/2; 433/24, 34
See application file for complete search history.

(56) References Cited

U.S. PATENT DOCUMENTS

| 5,879,158 | A | 3/1999 | Doyle et al. |
| 6,099,314 | A | 8/2000 | Kopelman et al. |
| 6,123,544 | A | 9/2000 | Cleary |
| 6,152,731 | A | 11/2000 | Jordan et al. |
| 6,322,359 | B1 | 11/2001 | Jordan et al. |
| 6,334,772 | B1 | 1/2002 | Taub et al. |
| 6,334,853 | B1 | 1/2002 | Kopelman et al. |
| 6,457,978 | B1 | 10/2002 | Cloonan et al. |
| 6,632,089 | B2 * | 10/2003 | Rubbert et al. ............. 433/24 |
| 6,664,986 | B1 | 12/2003 | Kopelman et al. |
| 6,695,613 | B2 | 2/2004 | Taub et al. |
| 6,697,164 | B1 | 2/2004 | Babayoff et al. |
| 6,722,880 | B2 * | 4/2004 | Chishti et al. ............. 433/24 |
| 6,733,289 | B2 | 5/2004 | Manemann et al. |
| 6,739,869 | B1 | 5/2004 | Taub et al. |
| 7,033,327 | B2 | 4/2006 | Raby |

(Continued)

FOREIGN PATENT DOCUMENTS

WO  WO 97/03622  2/1997

OTHER PUBLICATIONS

U.S. Appl. No. 10/734,323, "Method of Placing Orthodontic Brackets on Teeth in a 3D Virtual World," filed Dec. 12, 2003.

(Continued)

Primary Examiner—Paul L Rodriguez
Assistant Examiner—Eunhee Kim

(57) ABSTRACT

An orthodontic treatment planning system is described that models the effects of torque losses within an orthodontic archwire-appliance system when computing a predicted final occlusion for a dental arch. The treatment planning system models engagement of the archwire with the orthodontic appliances at each appliance position along the length of the archwire. The treatment planning system iteratively determines the twist angle of the archwire at each appliance position along the length of the archwire and incrementally adjusts the orientation and the position of each tooth based on the determined twist angles until the twist angle at each position along the archwire is within a defined tolerance of zero. When the twist angle at each position along the archwire is within a defined tolerance of zero, the archwire is relaxed and a 3D representation of the computed final occlusion of the dental arch may be displayed.

64 Claims, 20 Drawing Sheets

U.S. PATENT DOCUMENTS

| | | |
|---|---|---|
| 7,080,979 B2 | 7/2006 | Rubbert et al. |
| 2002/0015934 A1* | 2/2002 | Rubbert et al. ............... 433/29 |
| 2002/0042038 A1* | 4/2002 | Miller et al. .................. 433/24 |
| 2003/0163291 A1 | 8/2003 | Jordan et al. |
| 2003/0215764 A1 | 11/2003 | Kopelman et al. |
| 2003/0219692 A1 | 11/2003 | Kopelman et al. |
| 2003/0224316 A1 | 12/2003 | Marshall |
| 2004/0054304 A1 | 3/2004 | Raby |
| 2004/0072120 A1* | 4/2004 | Lauren ........................ 433/24 |
| 2004/0142297 A1 | 7/2004 | Taub et al. |
| 2004/0142298 A1 | 7/2004 | Taub et al. |
| 2004/0197727 A1* | 10/2004 | Sachdeva et al. ............. 433/24 |
| 2004/0209220 A1* | 10/2004 | Manemann et al. ........... 433/24 |
| 2007/0015104 A1 | 1/2007 | Wiechmann et al. |

OTHER PUBLICATIONS

U.S. Appl. No. 10/771,641, "Planar Guides to Visually Aid Orthodontic Appliance Placement with a Three-Dimensional (3D) Environment," filed Feb. 4, 2004.

U.S. Appl. No. 10/903,686, "Automatic Adjustment of an Orthodontic Bracket to a Desired Occlusal Height Within a Three-Dimensional (3D) Environment," filed Jul. 30, 2004.

U.S. Appl. No. 10/959,624, "Placing Orthodontic Objects Along an Archwire Within a Three-Dimensional (3D) Environment", filed Oct. 6, 2004.

U.S. Appl. No. 10/959,625, "Movement of Orthodontic Objects Along a Virtual Archwire within a Three-Dimensional (3D) Environment", filed Oct. 6, 2004.

* cited by examiner

COMPUTING FINAL OCCLUSION WITH RESPECT TO TORQUE LOSS IN A THREE-DIMENSIONAL VIRTUAL ORTHODONTIC SYSTEM

TECHNICAL FIELD

The invention relates to electronic orthodontics and, more particularly, computer-based techniques for assisting orthodontic diagnosis and treatment.

BACKGROUND

The field of orthodontics is concerned with repositioning and aligning a patient's teeth for improved occlusion and aesthetic appearance. For example, orthodontic treatment often involves the use of tiny slotted appliances known as brackets that are fixed to the patient's anterior, cuspid, and bicuspid teeth. An archwire is received in the slot of each bracket and serves as a track to guide movement of the teeth to desired orientations. The ends of the archwire are usually received in specialized appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shapes of the appliances, including the orientation of the slots of the appliances, are selected so that the slots are aligned in a flat-reference plane at the conclusion of treatment. Additionally, a resilient archwire is selected with an overall curved shape that normally lies in a flat reference plane.

When the archwire is placed in the slots of the brackets in a straight wire appliance system at the beginning of orthodontic treatment, the archwire is often deflected upwardly or downwardly and twisted positively or negatively from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

As can be appreciated, it is important for the practitioner using straight wire appliances to fix each bracket in the exact proper position on the corresponding tooth. If, for example, a bracket is placed too far in an occlusal direction on the tooth surface, the archwire will tend to position the crown of the tooth too close to the gingiva (gums) at the end of the treatment. As another example, if the bracket is placed to one side of the center of the tooth in either the mesial or distal direction, the resultant tooth orientation will likely be an orientation that is excessively rotated about its long axis.

The process of positioning and bonding the brackets to the patient's teeth requires considerable care, and requires the practitioner to visually determine the proper location of the brackets on the respective teeth. Often, in a technique known as indirect bonding, a practitioner determines bracket positions by the use of a ruler, protractor and pencil to measure and mark features on a plaster cast made from impressions of the patient's teeth. This process is often difficult to carry out with precision, and may be subjective in nature. Consequently, it is often difficult for the practitioner to ensure that the brackets are precisely positioned on the teeth at correct locations.

SUMMARY

In general, the invention is directed to an orthodontic treatment planning system that computes a final occlusion based on a proposed prescription that accounts for the effects of torque loss in an orthodontic archwire-appliance system. As used herein, the term "torque loss" refers to incomplete archwire expression (i.e., less than full relaxation of the archwire) or less than full engagement of the archwire in the slots of the appliances. Torque loss in an archwire-appliance system may result in a discrepancy between the intended final occlusion and the actual final occlusion resulting from a proposed prescription. When computing the final occlusion, the orthodontic treatment planning system accounts for torque loss at each appliance position along the archwire. The system may therefore achieve a more accurate prediction of the actual final occlusion, which would result from a full course of orthodontic treatment with the proposed prescription.

The treatment planning system may, for example, model engagement of an archwire within the slots of the appliances in an orthodontic archwire-appliance system. The system may determine a twist angle of the archwire at each appliance position along the length of the archwire. The treatment planning system may also incrementally adjust the position and orientation of each tooth based on the determined twist angles during each iteration until the twist angle at each position along the archwire is approximately equal to zero. When the twist angle at each position along the archwire is approximately equal to zero, the archwire is relaxed and a 3D representation of the computed final occlusion of the dental arch adjusted for the effects of torque loss may be displayed.

The invention may provide one or more advantages. For example, by accounting for torque losses and adjusting the orientation of each tooth prior to computing a final occlusion, the techniques may present a more accurate prediction of the final occlusion that would be achieved by a particular orthodontic treatment. In this manner, the techniques may allow an orthodontic practitioner to select and define an orthodontic treatment with greater confidence in the final occlusion that would be achieved by the treatment.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
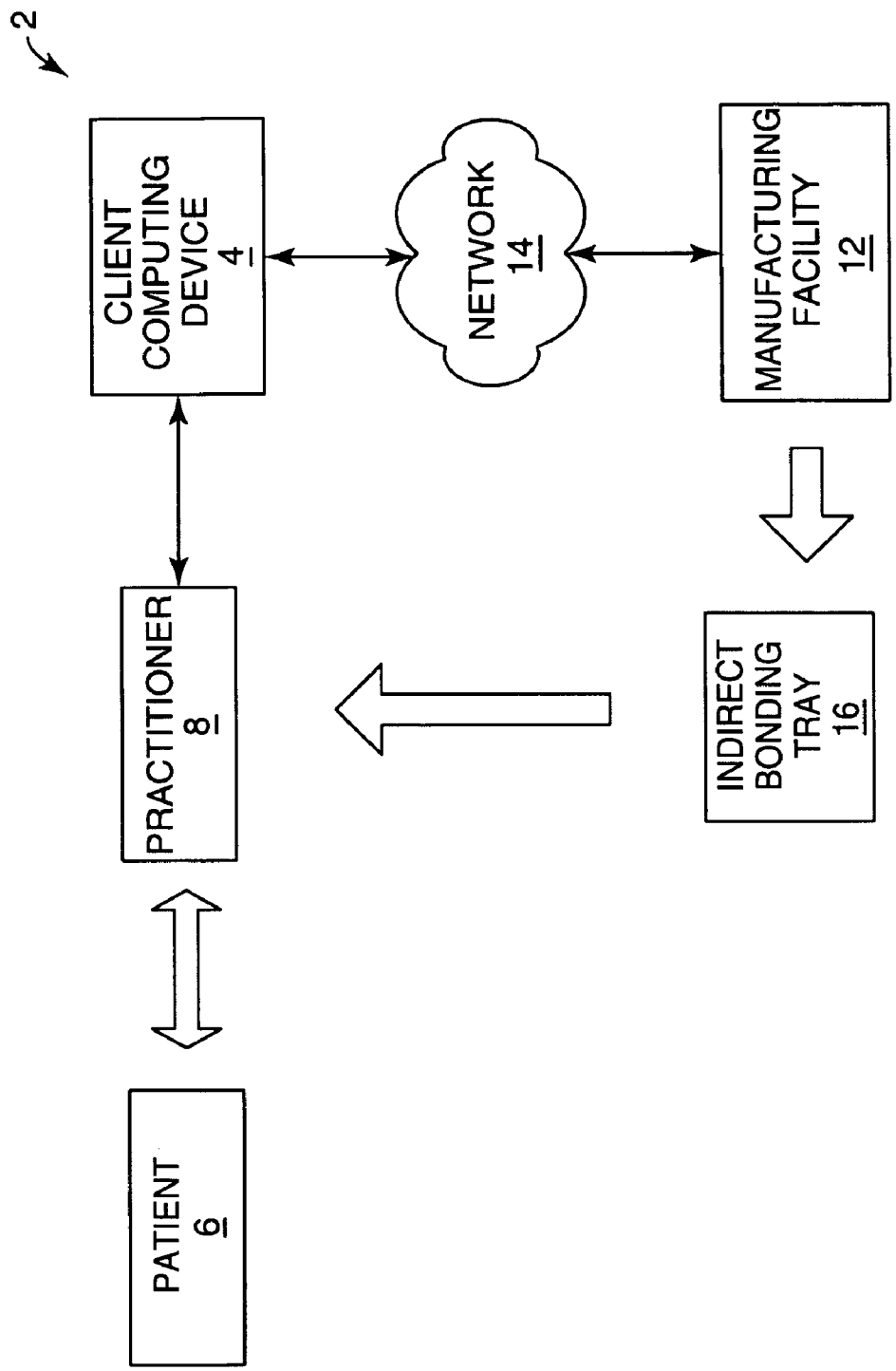
FIG. 1 is a block diagram illustrating an exemplary computer environment in which a client computing device computes a final occlusion for a dental arch taking torque loss into account.

FIG. 1 is a block diagram illustrating an exemplary computer environment 2 in which a client computing device 4 presents an environment for an orthodontic treatment planning system that computes a final occlusion based on a proposed prescription which accounts for the effects of torque loss in an orthodontic archwire-appliance system. As used herein, the term "torque loss" may refer to incomplete archwire expression (i.e., less than full relaxation of the archwire) or less than full engagement of the archwire in the slots of the appliances. Torque loss in an archwire-appliance system may result in a discrepancy between the intended final occlusion and the actual final occlusion resulting from a proposed prescription. Modeling software executing on client computing device 4 models engagement of the archwire at each appliance position along the archwire when computing the final occlusion. The system may therefore achieve a more accurate prediction of the actual final occlusion that would result from a full course of orthodontic treatment with the proposed prescription.

When computing the final occlusion, the modeling software may, for example, determine a twist angle of the archwire at each appliance position along the length of the archwire. The treatment planning system may also incrementally adjust the position and orientation of each tooth based on the determined twist angles until the twist angle at each position along the archwire is approximately equal to zero. When the twist angle at each position along the archwire is approximately equal to zero, the archwire is relaxed and a 3D representation of the computed final occlusion of the dental arch adjusted for the effects of torque loss may be displayed. The archwire may also be displayed at any point throughout the process with any twists present in it. The modeling software renders the 3D representation of the orthodontic objects to allow the practitioner to visualize the result.

For purposes of the present description, the term "appliance" shall be generally understood to mean orthodontic appliances such as brackets, buccal tubes, sheaths, or any other type of appliance of the type that may be coupled to an archwire. Also, although the text and drawings may at times refer to brackets, these references shall also be understood to encompass other types of appliances that may be coupled to an archwire.

A 3D representation of the dental arch before treatment may be initially generated by digitally scanning a physical dental impression of the teeth of patient 6, or by scanning a casting made from the impression. Alternatively, practitioner 8 may use an intraoral scanner to produce the 3D digital representation directly from the teeth of patient 6. Other methods of scanning are also possible.

Practitioner 8 interacts with client computing device 4 to view the 3D digital representation of the teeth and define a proposed orthodontic prescription by selecting "virtual" brackets that embody certain geometric attributes, then precisely positioning those brackets on individual teeth within the modeled dental arch. During this process, the modeling software manipulates each bracket and each tooth as a separate object within the 3D environment, and fixes the position of each bracket within the 3D space relative to a coordinate system associated with the bracket's respective tooth. Consequently, practitioner 8 is able to independently view and precisely locate each bracket within the 3D environment relative to its respective tooth.

By accounting for torque losses and adjusting the orientation of each tooth prior to computing a final occlusion, the techniques may present a more accurate prediction of the final occlusion that would be achieved by a particular orthodontic treatment. In this manner, the techniques may allow an orthodontic practitioner to select and define an orthodontic treatment (e.g., select and position brackets on the surface of each tooth) with greater confidence in the final occlusion that would be achieved by the treatment otherwise.

Once a proposed orthodontic prescription is determined, and the teeth are placed and displayed and the practitioner has indicated his or her approval, client computing device 4 communicates the bracket placement positions to manufacturing facility 12 via network 14. In response, manufacturing facility constructs an indirect bonding tray 16 for use in physically placing brackets on the teeth of patient 6. In other words, manufacturing facility 12 fabricates indirect bonding tray 16 based on the bracket placement positions selected by practitioner 8 within the 3D environment presented by client computing device 4. Manufacturing facility 12 may, for example, use conventional commercially available brackets selected by practitioner 8 to form indirect bonding tray 16. Manufacturing facility 12 forwards indirect bonding tray 16 to practitioner 8 for use in a conventional indirect bonding procedure to place the brackets on the teeth of patient 6.

Alternatively, client computing device 4 need not forward the bracket placement positions to manufacturing facility 12. Client computing device 4 may instead output, e.g., display or print, the relevant distances and angles for each bracket to assist practitioner 8 in manually positioning the brackets on the teeth of patient 6.

Figure 2:
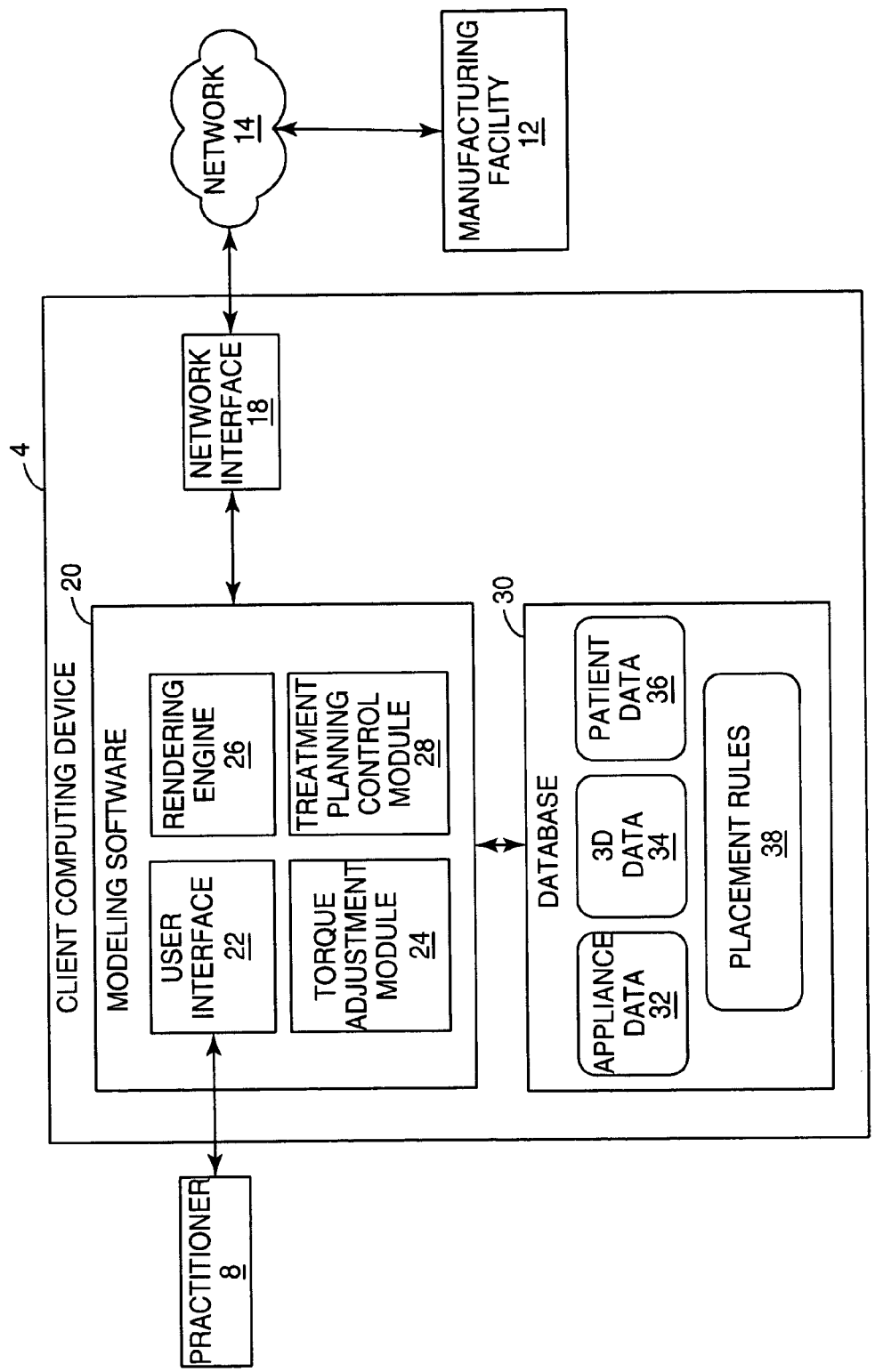
FIG. 2 is a block diagram illustrating an example embodiment of the client computing device of FIG. 1 in further detail.

FIG. 2 is a block diagram illustrating an example embodiment of client computing device 4 in further detail. In the illustrated embodiment, client computing, device 4 provides an operating environment for modeling software 20. As described above, modeling software 20 presents a modeling environment for modeling and depicting the 3D representation of the teeth of patient 6 (FIG. 1). In the illustrated embodiment, modeling software 20 includes a user interface 22, a torque adjustment module 24, a rendering engine 26 and a treatment planning control module 28.

User interface 22 provides a graphical user interface (GUI) that visually displays the 3D representation of the patient's teeth as well as 3D representations of the brackets. In addition, user interface 22 provides an interface for receiving input from practitioner 8, e.g., via a keyboard and a pointing device, for manipulating the orthodontic objects and placing or moving the brackets on respective teeth within the modeled dental arch. User interface 22 may also visually display a 3D representation of the patient's dental arch and/or of specified portions of the patient's dental arch.

Treatment planning control module 28 can be considered an interactive module for development of an orthodontic treatment plan, also referred to as a prescription. Because each orthodontic object, such as a bracket and a tooth, is a separate and independent virtual object, it can be moved freely relative to the other objects within the 3D virtual environment. Consequently, practitioner 8 can selectively position each virtual bracket on its respective virtual tooth. Treatment planning control module 28 may allow practitioner 8 to interactively position any of the orthodontic objects along any combination of X, Y and Z directions, as well as interactively rotate each orthodontic object about the X, Y and Z axes.

Practitioner 8 may select an individual orthodontic object for movement by, for example, clicking on a particular bracket, tooth or other orthodontic object, selecting a bracket number or tooth number from a drop-down or other menu, or by any other suitable means of selecting an object. User interface 22 includes navigational controls for positioning the orthodontic object.

Modeling software 20 interacts with database 30 to access a variety of data, such as appliance data 32, 3D data 34, patient data 36, and placement rules 38. Database 30 may be represented in a variety of forms including data storage files, lookup tables, or a database management system (DBMS) executing on one or more database servers. The database management system may be a relational (RDBMS), hierarchical (HDBMS), multi-dimensional (MDBMS), object oriented (ODBMS or OODBMS), object relational (ORDBMS) or other type of database management system. The data may, for example, be stored within a single relational database such as Oracle Database 10g from Oracle Corporation. Although illustrated as local to client computing device 4, database 30 may be located remote from the client computing device 4 and coupled to the client computing device 4 via a public or private network, e.g., network 14.

Appliance data 32 describes a set of commercially available brackets, archwires or other orthodontic appliances that may be selected by practitioner 8 and utilized within the 3D modeling environment. For example, appliance data 32 may store a variety of attributes for the commercially available brackets, such as dimensions, slot locations and characteristics, torque angles, angulations and other attributes. Appliance data 32 may also store dimensions and material properties for commercially available archwires. User interface 22 provides a menu-driven interface by which practitioner 8 selects the type of brackets and archwires for use in defining an orthodontic prescription for patient 6.

Patient data 36 describes a set of one or more patients, such as patient 6. For example, patient data 36 specifies general information, such as a name, birth date, and a dental history, for each patient. In addition, patient data 36 specifies a current prescription specified for each of the patients, including the types of brackets selected by practitioner 8 for use with each of the patients, and their associated positions and orientations on the teeth of patient 6.

The orthodontic industry has developed standard prescriptions for many commercially available orthodontic appliances. These standardized prescriptions generally tend to satisfy the functional and the aesthetic requirements for most patients. The standardized prescriptions may be used to achieve uniformity among patients or to avoid the more time consuming process of devising a custom set of metrics for each individual patient.

For some patients, a standardized set of metrics for the teeth in the dentition may be satisfactory. For other patients, practitioner 8 may desire to create a customized prescription to achieve a more aesthetically pleasing result, or to more adequately take into account that patient's malocclusion. As another example, a combination of standardized and customized prescriptions for different teeth in the dentition may be used. Practitioner 8 inputs the desired prescription via user interface 22, which is then stored in database 30 as patient data 36.

Placement rules 38 may specify industry-defined placement rules for commercially available appliances. In addition, placement rules 38 may include user-defined rules specified by practitioner 8 or other rules for controlling appliance placement. For example, one rule for certain commercially available brackets is to align the medial line or longitudinal axis of the bracket with the Facial Axis of the Clinical Crown (FACC) of the tooth. The FACC is defined as the curved line formed by the intersection of the mid-sagittal plane and the facial surface of the tooth. Another exemplary industry-defined placement rule is to place the center of a base of the bracket on the FACC of the tooth equidistant from the occlusal edge or occlusal-most point on the FACC and the gingival margin of the crown. This location is also known as the Facial Axis Point (FA Point).

As another example, practitioner 8 may desire to place brackets at a position that is different from the FA Point. Consequently, practitioner 8 may specify different prescriptions for different types of teeth in the dentition, for different types of brackets, or both. Optionally, the prescription may be based in whole or in part on known rules associated with a particular type of the appliances selected by practitioner 8. Rendering engine 26 accesses and renders 3D data 34 to generate the 3D view presented to practitioner 8 by user interface 22. More specifically, 3D data 34 includes information defining the 3D objects that represent each tooth and appliance within the 3D environment. Rendering engine 26 processes each object to render a 3D triangular mesh based on viewing perspective of practitioner 8 within the 3D environment. User interface 22 displays the rendered 3D triangular mesh to practitioner 8, and allows the practitioner to change viewing perspectives and manipulate objects within the 3D environment.

Orthodontic appliances, such as brackets, buccal tubes, sheaths, etc., may initially be placed in the 3D environment using any of several different methods.

For example, brackets may initially be placed in the 3D environment using the method described in commonly assigned U.S. Pat. No. 7,210,929, which is incorporated herein by reference in its entirety. Manual adjustment of orthodontic brackets may be assisted by use of visual planar guides, as described in copending and commonly assigned U.S. patent application Ser. No. 10/771,641, entitled "Planar Guides to Visually Aid Orthodontic Appliance Placement within a Three-Dimensional (3D) Environment", filed Feb. 4, 2004 to Raby, et al., which is incorporated herein by reference in its entirety. In that application, a system visually aids the user in manual placement of brackets through manual adjustments to bracket position and orientation. Other methods of placing or adjusting the position of brackets on the teeth may also be used. For example, a system for automatic adjustment of an orthodontic appliance to a desired occlusal height is described in copending and commonly assigned U.S. patent application Ser. No. 10/903,686, entitled "Automatic Adjustment of an Orthodontic Bracket to a Desired Occlusal Height Within a Three-Dimensional (3D) Environment", filed Jul. 20, 2004 to Raby, et al., which is incorporated herein by reference in its entirety. It shall be understood that these and/or any other techniques may be used to initially place the orthodontic appliances on the teeth in the 3D environment and thus determine the patient's prescription, and that the invention is not limited in this respect. Moreover, although described for purposes of illustration with respect to modeling software 20 executing on client computing device 4, any computing device, including servers remote from practitioner 8, may apply the techniques.

Once practitioner 8 has developed a proposed orthodontic prescription, torque adjustment module 24 computes a final occlusion for the proposed orthodontic prescription that accounts for the effects of any torque loss that may occur in the archwire-appliance system. Torque loss, e.g., incomplete archwire expression (i.e., less than full relaxation) or less than full engagement of the archwire in the slots of the appliances, may result in a discrepancy between the intended final occlusion and the actual final occlusion resulting from the proposed prescription.

Incomplete archwire expression may result in teeth that fail to move completely as intended by the orthodontic prescription developed for a patient. Because archwires move teeth by converting potential energy to kinetic energy over the duration of the treatment period (i.e., relaxing), any potential energy remaining in the archwire when the teeth have stopped moving is regarded as incomplete archwire expression. Such potential energy may be stored in the form of bends and twists in the archwire. Bends are due to both the displacement of brackets from their rest positions on the archwire and first- and second-order rotations of brackets from their rest orientations on the archwire. Twists are due to third-order rotations of brackets from their rest orientations on the archwire. Third-order rotations of brackets and teeth are commonly known as torques and move teeth by changing their angles of inclination with respect to the occlusal plane.

Less than full engagement of the archwire in the slots of the appliances may also result in teeth that fail to move completely as intended by the orthodontic prescription developed for a patient. For example, when an archwire of rectangular cross-section is used with brackets having rectangular archwire slots, this loss of expression may be due to ligatures failing to hold the archwire in the bottom of each slot (resulting in labio-lingual displacements or first-order rotations) or to tolerances between the archwire and the slot (resulting in labio-lingual and occluso-gingival displacements and second- and third-order rotations).

FIGS. 3A-3D are schematic diagrams that provide cross-sectional side views of orthodontic brackets and archwires in the slots of those brackets. When computing a final occlusion that takes torque loss into account, torque adjustment module 24 models engagement of the archwire in the slots of the appliances in the archwire-appliance system. When doing so, torque adjustment module 24 determines a "twist angle" of the archwire at every bracket location along its length.

FIGS. 3A-3D illustrate how the torque angle of a bracket and the twist angle of an archwire may be defined for purposes of the present description. In one embodiment, the torque angle of each bracket and the twist angle of the archwire at each point are referenced to the occlusal plane of the dental arch. For example, the torque angle of each bracket may be defined as the angle between the labio-lingual vector of the bracket slot (which in the examples of FIGS. 3A-3D extends parallel to and midway between the occlusal and gingival walls of the archwire slot 52) and a perpendicular projection of the labio-lingual vector onto the reference occlusal plane. Similarly, the "twist angle" of the archwire may be defined as the angle between the labio-lingual vector of the archwire (which in the examples of FIGS. 3A-3D extends parallel to and midway between the occlusal and gingival sides of the archwire 54) and a perpendicular projection of the labio-lingual vector onto the reference occlusal plane.

Figure 3A:
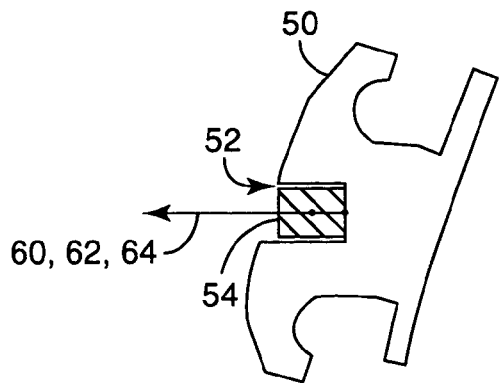
FIGS. 3A-3D illustrate the archwire twist angle with respect to the reference occlusal plane, the bracket torque angle with respect to the reference occlusal plane, and the relative difference between the archwire twist angle and the bracket torque angle that determine the "slop zone" of an individual bracket.

FIG. 3A illustrates a cross-section of an orthodontic bracket 50 with an archwire 54 in bracket slot 52. In FIG. 3A, the labio-lingual axis 62 of bracket slot 52 is parallel to the reference occlusal plane 60. The torque angle of the example bracket 50 as measured with respect to the occlusal plane 60 shown is therefore equal to zero. In addition, the labio-lingual axis 64 of archwire 54 is also parallel to the reference occlusal plane 60 and is, therefore, also parallel to the labio-lingual axis 62 of bracket slot 52. In other words, in this example, archwire 54 is not twisted with respect to bracket slot 52, and archwire 54 is said to be fully engaged in bracket slot 52. The twist angle of the archwire is, therefore, zero degrees in this example.

Figure 3B:
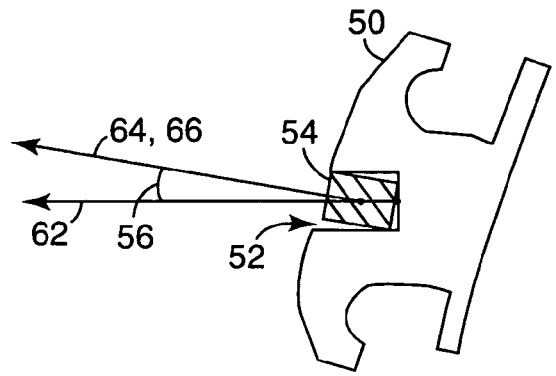
Figure 3C:
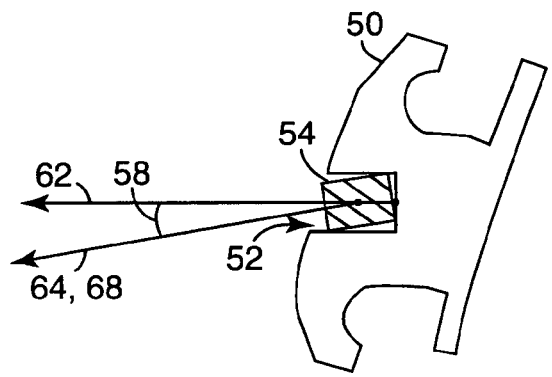

FIGS. 3B and 3C illustrate two examples of archwire 54 twisting within bracket slot 52. As illustrated, archwire 54 may twist in either the positive or negative directions within positive torque limit 66 and negative torque limit 68 of the archwire 54. These positive and negative torque limits 66 and 68 are defined as the twist angle within each bracket slot where the archwire first engages the bracket slot. The positive and negative torque limits 66 and 68 represent the maximum twist angle that the labio-lingual axis of the archwire can make with the labio-lingual axis of the bracket slot. The archwire can have a twist angle anywhere within the range defined by the positive and negative torque limits 66 and 68. In FIG. 3B, the labio-lingual axis 64 of archwire 54 is shown at the positive torque limit 66. Similarly, in FIG. 3C, the labio-lingual axis 64 of archwire 54 is shown at the negative torque limit 68. In both FIG. 3B and FIG. 3C, the archwire 54 is also said to form a couple with bracket slot 52, because equal and opposite forces occur at two points displaced by equal radii from the centroid of an archwire 54 cross-section.

In the examples shown in FIGS. 3B and 3C, the positive and negative torque limits 66 and 68 have substantially the same magnitude. However, the positive and negative torque limits 66 and 68 need not have the same magnitude. For example, the neutral point may be biased toward either the positive or the negative torque limit 66 or 68 depending upon the shape of the bracket slot 52 and the shape of the archwire 54. In addition, the magnitude of positive and negative torque limits 66 and 68 may vary depending on the torque angle of bracket 50, the size and shape of bracket slot 52 and the size and shape of archwire 54. For example, the top and bottom surfaces of bracket slot 52 need not be parallel. Similarly, archwire 54 may take on any number of shapes, including square, rectangular, trapezoidal, parallelogram, oval, elliptical, or virtually any other shape. Furthermore, the positive and negative torque limits 66 and 68 may be different for each tooth in a dental arch. Because an orthodontic prescription may specify different brackets having different torque angles for each tooth in the dentition, the torque limits 68 and 69 for each tooth may also vary across the dentition.

In addition, it shall be understood that the term "slot" can be a passage with four walls, as found in buccal tubes and sheaths, a passage with three walls that is open along one side, as found in conventional brackets with tiewings, as well as a passage with three fixed walls and a fourth full or partial wall that can be opened, as found in self-ligating brackets.

The area between the positive and negative torque limits of the archwire within each bracket slot may be referred to herein as the "slop limits" or "slop zone." Essentially, the slop zone defines the amount that an archwire may twist within the bracket slot until archwire engagement begins (i.e., until a couple is formed). In other words, an archwire may twist within the bracket slot 52 within the slop zone without necessarily engaging the bracket. In the example of FIGS. 3B and 3C, the positive and negative torque limits of the archwire 54 are approximately +9.6 degrees and −9.6 degrees, respectively. Although in this example the positive and negative torque limits have the same magnitude, in other embodiments the positive and negative torque limits may have different magnitudes.

Figure 3D:
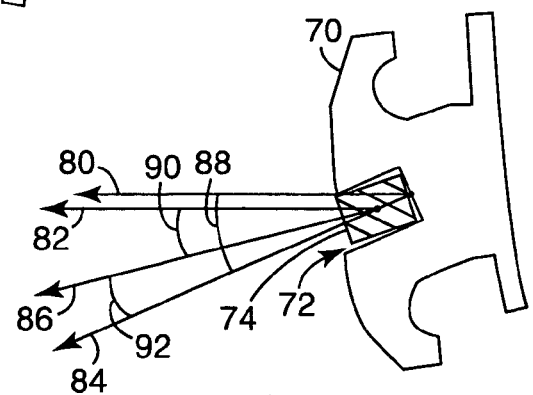

FIG. 3D illustrates another example of a bracket 70 having a bracket slot 72 and an archwire 74. The exemplary bracket 70 has a torque angle 88 defined by the angle that labio-lingual axis 84 of bracket slot 72 makes with reference occlusal plane 80. In this example, torque angle 88 of bracket 70 is −24.2 degrees. Also, archwire 74 may twist within bracket slot 72. Angle 90 is the angle that labio-lingual axis 86 of archwire 74 makes with reference occlusal plane 82. In the example shown in FIG. 3D, angle 90 is −14.6 degrees. The negative torque limit 92 in this example, i.e., the maximum amount that archwire 74 may twist in the negative direction before engaging bracket 70, is approximately −9.6 degrees (−24.2−(−14.6)=−9.6). Assuming that the positive torque limit is equal in magnitude of the negative torque limit 92, the total magnitude of the slop zone will be approximately 19.2 degrees (+9.6−(−9.6)=19.2). In this particular example, archwire 74 is twisted to the torque limit of bracket slot 72, thus causing archwire 74 to engage bracket 70, also forming a couple.

Figure 4:
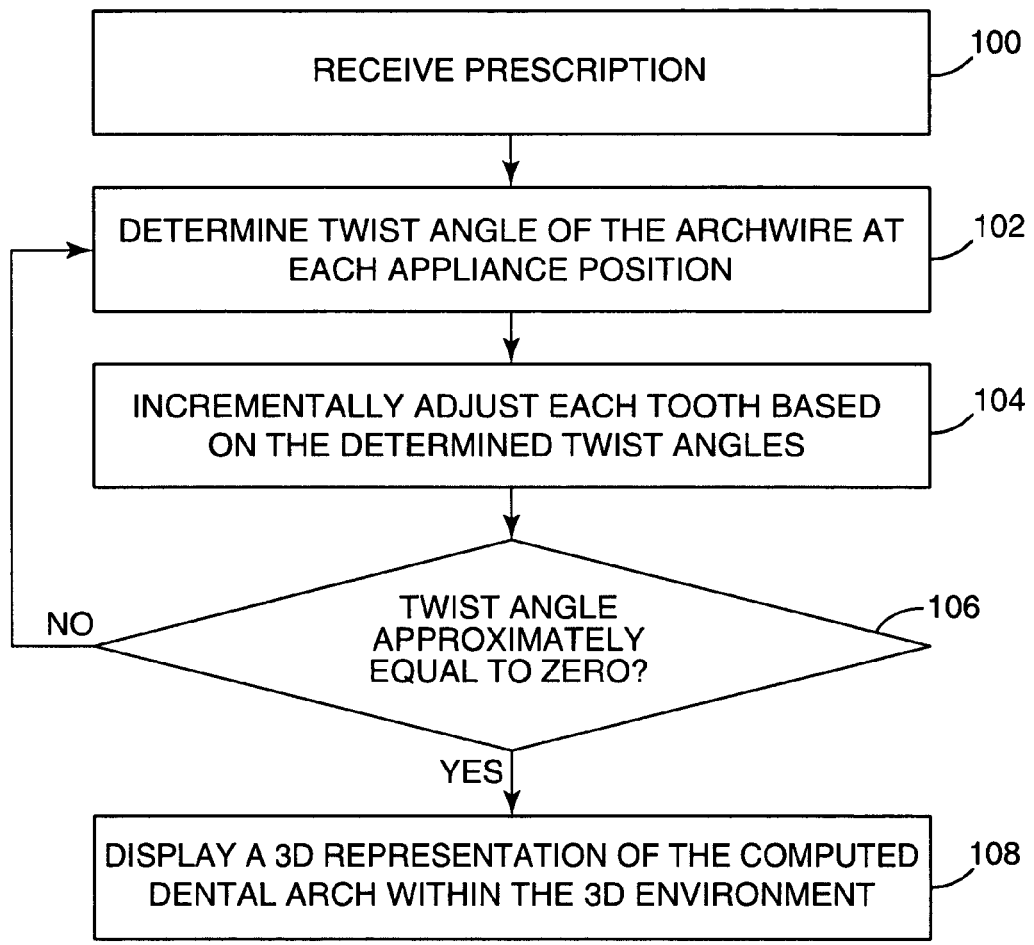
FIG. 4 is a flowchart illustrating exemplary operation of modeling software executing on the client computing device to compute a final occlusion adjusted for the effects of torque loss on an orthodontic appliance system.

FIG. 4 is a more detailed flowchart illustrating an example of the overall operation of torque adjustment module 24. More specifically, the flowchart of FIG. 4 illustrates operation of torque adjustment module 24 computing a final occlusion that accounts for torque loss in an archwire-appliance system and rendering a 3D representation of the computed final occlusion within the 3D environment.

Initially, torque adjustment module 24 receives a proposed orthodontic prescription for a dental arch in malocclusion (100). The orthodontic prescription may be stored in database 30 as part of appliance data 32 and patient data 36. The prescription may include a set of torque angles, the types of brackets selected by practitioner 8 for use with patient 6, and their associated set of positions and orientations on the teeth of patient 6. Torque adjustment module 24 determines the twist angle of the archwire at each appliance position along the length of the archwire (102). The algorithm used by torque adjustment module 24 to determine the twist angle at each position bracket position along the archwire is described in greater detail herein with respect to FIGS. 6A-6H and 7A-7B.

Based on the determined twist angles, torque adjustment module 24 incrementally adjusts the orientation and position of each tooth to simulate the calculated torques acting on each tooth/appliance over a small period of time (104). After the orientation and position of each tooth in the dental arch is incrementally adjusted, torque adjustment module 24 checks whether the twist angle of the archwire is approximately equal to zero at each appliance position along the archwire (106). If the twist angle of the archwire is not approximately equal to zero at each position along the length of the archwire, torque adjustment module 24 prepares for the next iteration and determines the twist angle of the archwire at each of the adjusted bracket positions along the archwire (102). This process of iteratively determining the twist angles of the archwire and incrementally adjusting the orientation and position of the appliances continues until the twist angle of the archwire is approximately equal to zero at each appliance position along the length of the archwire. Once all of the twist angles of the archwire are approximately equal to zero at each bracket, the archwire is "relaxed". At this point, torque adjustment module 24 assumes that no further movement of the teeth will occur. Torque adjustment module 24 may then display a 3D representation of the computed final occlusion for the dental arch within the 3D environment (108). Alternatively, the resultant torque angle of each bracket may be displayed in a table or may be stored or presented in any other suitable manner.

Thus, torque adjustment module 24 iteratively determines the twist angle of the archwire at each bracket position along the length of the archwire and incrementally adjusts the orientation and position of each tooth based on the determined twist angles until the twist angle at each position along the archwire is approximately equal to zero. In this manner, torque adjustment module 24 may be viewed as iteratively computing a final occlusion for the dental arch in a manner that models torque loss present within the modeled orthodontic treatment. When the twist angle at each position along the archwire is approximately equal to zero, the archwire is fully relaxed, and rendering engine 26 generates a 3D representation of the final occlusion adjusted for torque loss as a visual aid to practitioner 8. Additionally, torque adjustment module 24 may also animate the adjustment of the dental arch of patient 6 from the initial malocclusion to the computed final occlusion in the 3D environment to further aid practitioner 8.

Specifically, torque adjustment module 24 may also render the 3D virtual archwire in the initial malocclusion or any intermediate malocclusion, illustrating geometrically the twist angle of the archwire at every point along its length (i.e., not just rendering the brackets at similar torque angles). Further, torque adjustment module 24 may assign color information to 3D data 34 such that the archwire in the initial malocclusion or any intermediate malocclusion is rendered in varying color (or intensity of grayscale or monochrome color) along its length as a function of the torsional stress at each lengthwise point. Similarly, torque adjustment module may render 3D virtual brackets that engage the archwire (i.e., form couples with the archwire) in a different color (or intensity of grayscale or monochrome color) than brackets that do not engage the archwire. In these ways, practitioner 8 may clearly visualize, throughout the period of archwire relaxation and resultant appliance movements, how the archwire twists along its length, the magnitude of torsional stress in each archwire segment, and which brackets engage (and do not engage) the archwire.

Visualization of the final occlusion for the dental arch enables practitioner 8 to compare a computed final occlusion of a proposed prescription with an adjusted final occlusion that takes the effects of torque loss into account. This further enables practitioner 8 to determine whether the received proposed orthodontic prescription will achieve an acceptable functional and/or aesthetic result given the effects that torque loss will have on the proposed prescription. Practitioner 8 may decide more accurately, based on the displayed adjusted final occlusion, to change or modify the proposed orthodontic prescription for certain ones or for all of the brackets to achieve an improved functional or aesthetic result. Practitioner 8 may modify the proposed prescription and view the simulated final occlusion until an acceptable result is achieved. By allowing practitioner 8 to visualize the final occlusion for a proposed prescription, and/or by allowing practitioner 8 to modify the proposed prescription until an acceptable functional and aesthetic result is achieved, bracket rebonding resulting from inaccurate bracket placement may be reduced and treatment time may be minimized.

Figure 5:
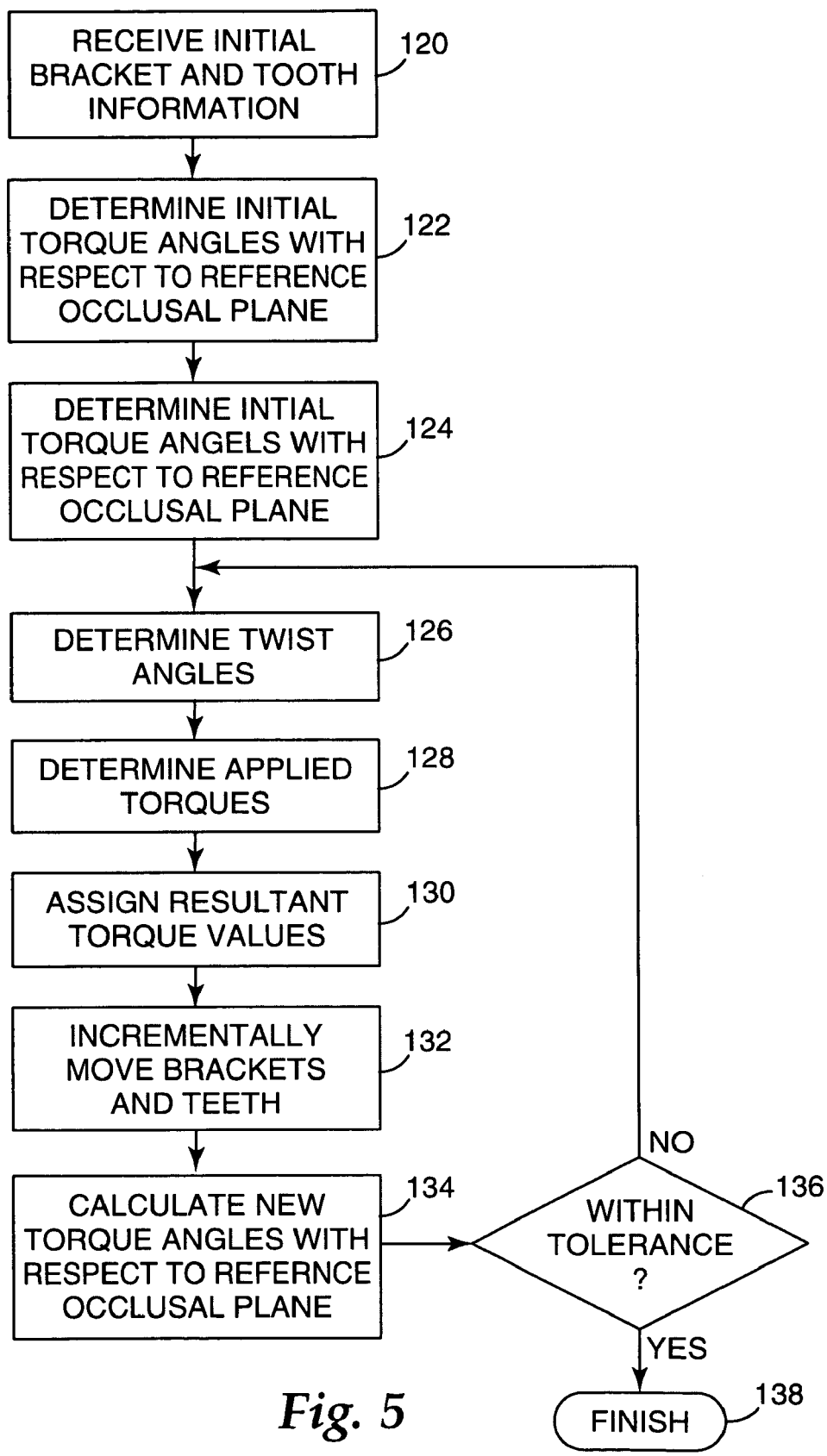
FIG. 5 is a more detailed flowchart illustrating exemplary operation of modeling software executing on the client computing device that considers torque loss in computing a final occlusion for a proposed orthodontic prescription.

FIG. 5 is a more detailed flowchart illustrating exemplary operation of torque adjustment module 24. Torque adjustment module 24 receives data defining the selected prescription, including a position of each bracket along with their defining metrics, including the prescribed torque angle for each bracket (120). Torque adjustment module 24 also determines the initial torque angle for each bracket with respect to a reference occlusal plane (122). To do this, torque adjustment module 24 defines a reference occlusal plane that is used to define the torque angle of each bracket and the twist angle of the archwire at every point along its length. The 3-dimensional (x, y, z) location of each bracket, according to its slot origin, is considered relative to the locations of all other brackets in an arch at the outset of treatment (an arch in malocclusion). Because these locations may roughly approximate a plane, a least-squares method of data fitting may be used to fit a plane to the set of 3-dimensional points. The torque angle of each bracket is then defined as the angle between the labio-lingual vector of the bracket slot and a perpendicular projection of the labio-lingual vector onto the reference occlusal plane. The term "torque angle" in this embodiment does not include any geometry that may be inherent in the design of the bracket, such as a relative angle between the slot coordinate system and the base coordinate system. Rather, it is the angle between the bracket slot and the reference occlusal plane. In another embodiment, the torque angle may be defined by finding the mean of the bracket slot vectors and defining the torque angle of each bracket as the angle between each bracket slot vector and the mean vector. Other methods of determining the torque angle may also be used.

Torque adjustment module 24 applies a scalar weight to each bracket that reflects the relative resistance to movement of the bracket's associated tooth (124). In one embodiment, for example, torque adjustment module 24 may estimate a tooth's resistance to movement based on its overall root surface area, a root profile area of the associated tooth, root length of the associated tooth, or the number of roots in the associated tooth. A heuristic may be used to assign integral weights based on one or more of these factors, coarsely approximating its resistance to movement, such as 1 for incisors and cuspids, 2 for bicuspids, and 3 for molars, for example. Other weighting schemes, including fractions or other weighting methods, can be used when more data is available on a tooth's root area or resistance to movement. Vector weights may also be used, where the resistance to movement differs depending on the direction of the force. It shall be understood, therefore, that there are several implementations for applying weights to each bracket, and that the invention is not limited in this respect.

Torque adjustment module 24 next determines the twist angle of the archwire at each bracket position along the length of the archwire (126). In one embodiment, the twist angles are determined using an iterative process described in detail below with respect to FIGS. 6A-6H and 7A-7B. Determination of the twist angle is based on the relative distance between each bracket along the archwire, the torque angle of each bracket with respect to the reference occlusal plane, and the positive and negative torque limits of the archwire within each bracket slot where engagement begins (also referred to as the "slop limits" or "slop zone"—see FIGS. 3A-3D and accompanying description). These torque limits may be based on the nominal cross-sectional width and height of the archwire, the radius of any chamfer that might be applied to the corners of the cross-section, and the nominal height of the archwire slot in each bracket. Additionally, the radius of curvature of the archwire to meet the form of the patient's arch may be considered to more accurately define the torque limits.

The algorithm by which torque adjustment module 24 determines the twist angle at each bracket along the length of the archwire is based on certain fundamental principles of mechanics. One such principle is that a bar of uniform cross-section in torsion (i.e., a shaft) experiences an applied torque between two couples that is proportional to the angle of twist between those two couples and inversely proportional to the distance between them. Another is that the torsional energy in the shaft is the sum of the differential energies in the shaft at each increment of twist angle between zero and the final twist angle. Another is that the total torsional energy in the shaft is the sum of the torsional energies in segments of shaft between couples. Yet another is that if the distance between couples remains constant, the change in twist angle in every segment approaches zero as the total torsional energy approaches zero (i.e., as the shaft relaxes with respect to torsion).

Torque adjustment module 24 determines the applied torque on each bracket (128). Applied torque is based on the twist angle of the archwire at every point along its length, along with the dimensions and material properties of the archwire. The applied torque at each bracket and resistance to movement (resistance weight) of a tooth associated with each bracket (i.e., reaction torque) are treated as signed torque values. Torque adjustment module 24 then assigns a resultant torque value to each bracket (130) based on the corresponding applied torque and resistance weight. Such torque values translate into forces on the roots of the teeth and eventually lead to tooth movement. As used in the following paragraphs, the term "couple" refers to equal and opposite forces that occur at two points of contact displaced by equal radii from the centroid of an archwire cross-section. A pair of couples may be located at adjacent appliance positions along the archwire or may have intervening appliances between them.

To assign the resultant torque values to each bracket, torque adjustment module utilizes the following parameters:

$\phi$: total angle of twist,

T: applied torque,

G: shear modulus of elasticity, $I_p$: polar moment of inertia, and

L: length of archwire segment between couples.

Applied torque is defined as $$T = \frac{\phi G I_p}{L}.$$

The polar moment of inertia with respect to an axis O, that is perpendicular to the cross-section of the archwire (i.e., an axis tangent to the archwire), is defined as $$I_p = \int_A \rho^2 \, dA,$$

where A is the cross-sectional area of the archwire, and $\rho$ is the distance from point O to a differential element of area dA. According to the parallel-axis theorem for polar moments of inertia, $$I_p = I_x + I_y.$$

For an archwire of rectangular cross-section, $$I_x = \frac{bh^3}{12}$$
$$I_y = \frac{hb^3}{12}.$$

Therefore, $$I_p = \frac{bh^3}{12} + \frac{hb^3}{12} = \frac{bh}{12}(h^2 + b^2).$$

Torsional energy in a segment of archwire is defined as $$E_T = \int T d\phi$$

This is the sum of the differential energies $Td\phi$, defined by a length L of archwire that is twisted in increments $d\phi$ over an interval of twist angle $\phi$. Specifically, $$E_T = \int \frac{\phi G I_p}{L} d\phi = \frac{G I_p}{L} \int \phi d\phi = \frac{G I_p \phi^2}{2L}.$$

So, $$E_T = \frac{G I_p \phi^2}{2L}.$$

Total torsional energy in an archwire divided into n segments by n+1 couples:

$$E_T = \frac{G I_p}{2} \sum_i^n \frac{(\phi_{i+1} - \phi_i)^2}{L_i}.$$

There may be n+1 or n+2 segments if the archwire extends beyond one or both terminal couples, respectively. In such cases, these segments of archwire are not twisted, because two couples are required to twist a segment of wire. Therefore, these segments contribute no torsional energy, and are not included in the sum.

The use of $\phi$ in this equation is slightly different than in the general form above. In the general form, $\phi$ is used by itself to denote the total angle of twist between the two couples at opposite ends of the archwire segment. Here, $\phi_i$ and $\phi_{i+1}$ are used to denote the angle of twist of the archwire at each couple relative to a given coordinate system, such as a reference occlusal plane. The total angle of twist in each segment i, therefore, is the difference between twist angles $\phi_i$ and $\phi_{i+1}$.

Note also that if the distance between couples remains constant, the change in twist angle in every segment approaches zero as the total torsional energy approaches zero:

$$\forall i, \phi_i \to 0 \text{ as } E_T \to 0.$$

This is the nature of relaxation of an archwire.

For example, suppose a stainless steel archwire has a shear modulus of elasticity $$G = 75 \text{ GPa} = 75 \times 10^9 \text{ Pa},$$

and a uniform rectangular cross-section of 0.018 in.×0.022 in. Converting height h and width b from inches to meters gives:

$$h = 0.018 \text{ in.} = 0.4572 \times 10^{-3} \text{ m, and}$$

$$b = 0.022 \text{ in.} = 0.5588 \times 10^{-3} \text{ m.}$$

This results in a polar moment of inertia of $$I_p = \frac{bh}{12}(h^2 + b^2) = \frac{(0.5588 \times 10^{-3})(0.4572 \times 10^{-3})}{12}$$
$$[(0.4572 \times 10^{-3})^2 + (0.5588 \times 10^{-3})^2] = 1.110 \times 10^{-14} \text{m}^4$$

about the centroid of the cross-section when the axis of twist is along the archwire.

Assuming a total twist angle of $$\phi = 20° = 0.349 \text{ rad}$$

and a segment length between couples of $$L = 10 \text{ mm} = 10 \times 10^{-3} \text{ m,}$$

a torsional energy in the segment can be computed as:

$$E_T = \frac{G I_p \phi^2}{2L} = \frac{(75 \times 10^9)(1.110 \times 10^{-14})(0.349)^2}{2(10 \times 10^{-3})} = 5.1 \times 10^{-3} J = 5.1 \text{ mJ},$$

which results in $$E_T = 5.1 \text{ mJ}.$$

If the direction and magnitude of movement of each tooth is assumed proportional to the magnitude of the resultant torque value over a small interval of time, then the future torque angles of all brackets can be computed in a single iteration (corresponding to a small interval of time). The position and orientation of the brackets and the teeth are incrementally adjusted to simulate the action of the resultant torques on the brackets/teeth over an incrementally small, defined period of time (132). New bracket torque angles with respect to the reference occlusal plane for the brackets/teeth in the new positions can be redefined according to their respective degrees of movement (134). Over a period of many iterations, the archwire will eventually relax, reducing the twist angle in every segment to zero. In one embodiment, after each iteration during which the new torque angles are calculated, torque adjustment module 24 finds the minimum and maximum torque angle at each bracket along the archwire. If the difference between these two angles is less than or equal to the size of the slop zone plus a defined tolerance (e.g., 0.001 degrees or other defined tolerance) (136), torque adjustment module 24 determines that the archwire will no longer act to move the brackets (138) (i.e., the archwire is relaxed). In another embodiment, torque adjustment module 24 may cease movement of one or more brackets when the resultant torque on that bracket diminishes to a threshold torque value. The bracket's threshold torque value may be defined as a function of the resistance to movement of the tooth associated with said bracket. This represents the idea that the archwire-appliance system generally must overcome an initial torsional stress before a tooth starts moving. Thus, a residual torsional stress (twist angle) may be present in the archwire at the conclusion of treatment.

Because the torque angle of each bracket changes when either the archwire engages the bracket at its torque limits or the twist angle of the archwire changes, the brackets will come to rest at various torque angles that deviate from zero when the archwire comes to rest at a twist angle of zero along its entire length. These varied torque angles define a more accurate final occlusion than would otherwise be predicted by assuming full engagement of the archwire in the slot of every bracket.

In another embodiment, if minimum threshold torque values are known beyond which tooth movement ceases, then a final occlusion may be computed by terminating bracket movements at these thresholds and recording their torque values. The torque values of all brackets may also be recorded at any time during the treatment period and used to compute final occlusion.

Figure 6A:
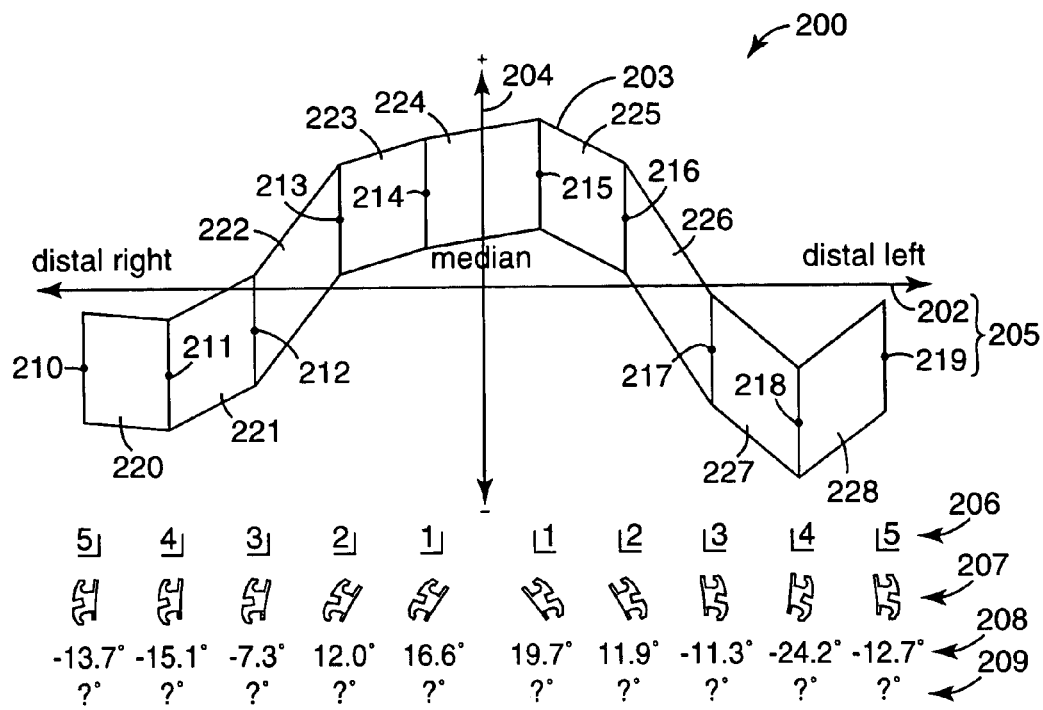
FIGS. 6A-6J are diagrams illustrating the method by which torque adjustment module 24 determines twist angles at each appliance position along the length of an archwire; and determines the applied torque at each anchor point.

FIGS. 6A-6H are diagrams illustrating one method by which torque adjustment module 24 determines twist angles at each appliance position along the length of an archwire. FIG. 6A generally illustrates a representation of an example archwire-appliance system 200 for a dental arch in malocclusion. The example archwire-appliance system 200 shown in FIG. 6A corresponds to a patient's dental arch at one specific point in time during the course of orthodontic treatment. The vertical axis 204 represents the midline of the dental arch. The horizontal axis 202 represents the mean occlusal plane of the dental arch. References to "right" and "left" in the drawings and in the corresponding text as used herein are with respect to the patient's right and left in the manner commonly used in the dental arts. Archwire-appliance system 200 may be referred to as the "root" appliance system, because it encompasses the archwire-appliance system for the entire dental arch.

The torque angle for each bracket relative to the reference occlusal plane is illustrated by reference numerals 210-219. The numerical value of the torque angle for each bracket is shown in the second to last row of the Figures as indicated generally by reference numeral 208. For example, reference numerals 214 and 215 represent the torque angles of the brackets corresponding to the right and left anterior-most teeth, and have corresponding numerical values of 16.6 degrees and 19.7 degrees, respectively. Similarly, reference numerals 210 and 219 represent the torque angles of the brackets corresponding to the right and left posterior-most teeth, and have corresponding numerical values of −13.7 degrees and −12.7 degrees, respectively, in this example.

The horizontal axis 202 allows the relative distance between the origin of a coordinate system for each bracket and the median line 204 of the dental arch to be indicated. In the example shown in FIGS. 6A-6H, for simplicity of illustration, all adjacent brackets throughout the dental arch are assumed to be the same distance apart. However, it shall be understood that these distances can vary across the dental arch, and that the invention is not limited in this respect.

A vertical line extending through the prescribed torque angle at each position represents the slop zone for each bracket. For example, reference numeral 205 represents the slop zone for the bracket at appliance position 219. As described above, the slop zone represents the degree to which the archwire may twist within the bracket slot, bounded by the positive and negative torque limits for each particular archwire-bracket combination (see FIGS. 3A-3D). The slop zone 203 of the entire dental arch is shown in FIG. 6A as bounded by a series of lines connecting the positive torque limits of adjacent brackets across the dental arch and by a series of lines connecting the negative torque limits of adjacent brackets across the dental arch.

In this example, for simplicity of illustration, the magnitudes of the slop zones are the same for each appliance position in the dental arch. However, it shall be understood that the magnitude of the slop zones can vary across the dental arch, and that the invention is not limited in this respect. Also, the positive and negative torque limits are the same for each appliance position in the dental arch. Again, it shall be understood that the positive and negative torque limits need not have the same magnitude on any particular bracket, nor are the positive and negative torque limits required to have the same magnitude across for all appliances (i.e., brackets) in the archwire-appliance system.

To determine the twist angle at each appliance position along the archwire, torque adjustment module 24 determines each position where the archwire actually engages a bracket. Each of these positions is designated an "anchor point." Due to the effects of torque loss on the archwire-appliance system, such as incomplete archwire expression and less than full engagement of the appliances, the archwire may not actually fully engage each appliance in an archwire-appliance system at all times during the course of orthodontic treatment. Therefore, not every appliance position along the archwire will be necessarily be an anchor point. In order to model the effects of torque losses in an archwire-appliance system, torque adjustment module 24 computes the actual engagement positions (i.e., "anchor points") at each point in time throughout treatment. Once the anchor points for a specific point in time are determined, torque adjustment module 24 computes the archwire twist angles at each position along the archwire. Torque adjustment module 24 then determines the resultant torque on each bracket/tooth. Torque adjustment module 24 incrementally adjusts the brackets and/or the associated teeth to simulate the resultant applied torques acting on each bracket/tooth for an incrementally small, defined period of time. Then, based on the new applied torques, torque adjustment module 24 recalculates new anchor points for the current archwire-appliance system. As the iterative adjustment process continues, the modeled archwire eventually flattens out, i.e., relaxes, as the twist angle of the archwire approaches zero at each appliance position along the length of the archwire.

The following paragraphs describe the process carried out by torque adjustment module 24 to determine the twist angles of an archwire at each appliance position along the length of the archwire. It shall be understood that the following process may be carried out hundreds or thousands of times during the iterative adjustment process. The number of iterations may be varied to achieve the desired level of accuracy in computing the final occlusion with the effects of torque losses taken into account.

Figure 6B:
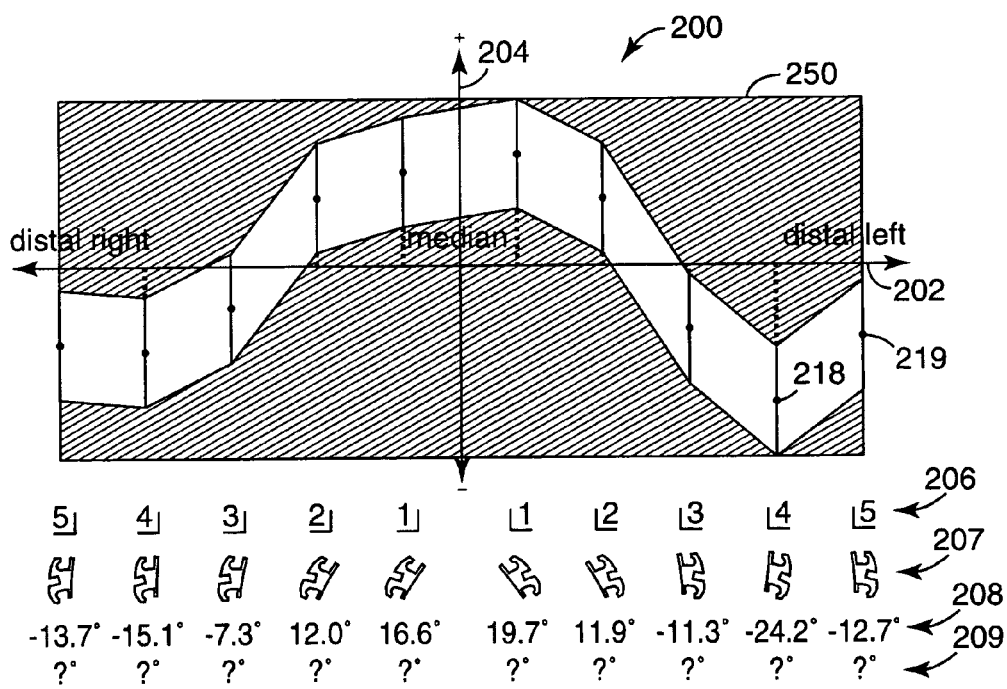
Figure 6C:
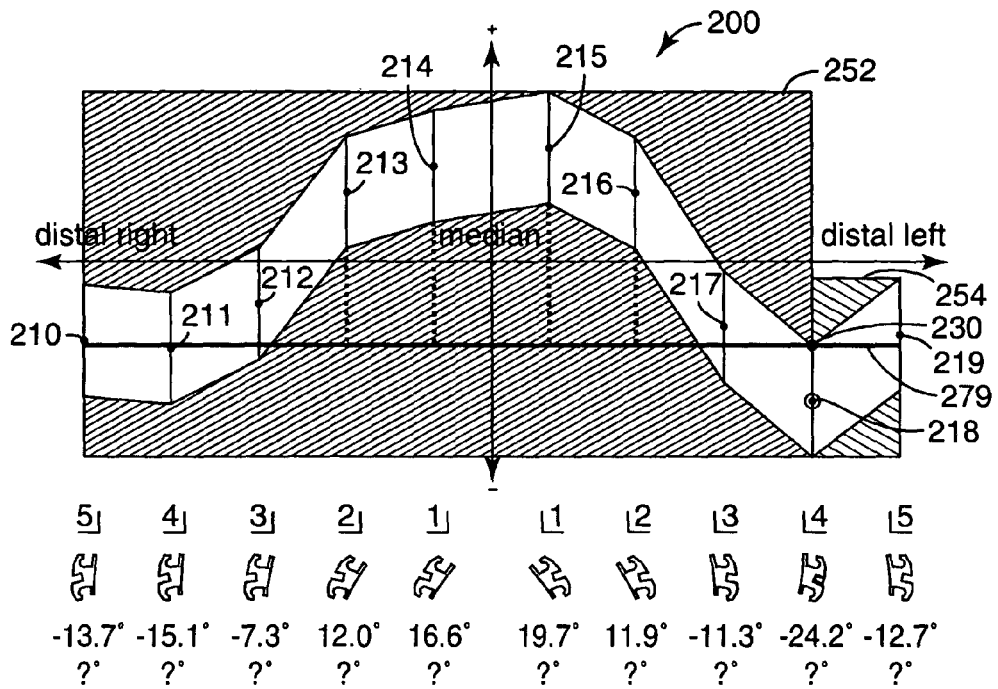

FIG. 6B is a diagram illustrating one embodiment of how torque adjustment module 24 may identify a first "anchor point" in the exemplary archwire-appliance system 200. Torque adjustment module 24 may first identify the appliance position having a torque angle that has the maximum deviation from an initial reference line (the "maximum deviator"). In one embodiment, the initial reference line is the horizontal line 202 representing the mean occlusal plane. In this example, the appliance position with the torque angle having the maximum deviation from the initial reference line 202 is appliance position 218. In FIG. 6C appliance position 218 is circled to indicate that it has an associated anchor point.

Torque adjustment module 24 next determines the "anchor point" for the identified appliance position. Specifically, torque adjustment module determines whether the archwire engages position 218 at the positive or negative torque limit of its corresponding slop zone. Torque adjustment module 24 selects an anchor point at the positive torque limit of a slop zone if the anchor point lies below the current reference line and selects the anchor point at the negative torque limit of the slop zone if the anchor point lies above the current reference line. In this example, torque adjustment module 24 selects the anchor point at the positive torque limit 230 of the corresponding slop zone because position 318 lies below current reference line 202.

Once a new anchor point is identified, torque adjustment module 24 divides the archwire-appliance system 250 into two separate appliance systems, right appliance system 252 and a left appliance system 254. The right and left appliance systems are shown in FIG. 6C. In this example, therefore, appliance system 250 may be referred to as the "parent" appliance system for right and left appliance systems 252 and 254, respectively.

Torque adjustment module 24 determines whether anchor point 230 is a right most appliance position of the root appliance system. A new horizontal reference line 279 is generated based on anchor point 230. In this example, therefore, torque adjustment module 24 determines whether reference line 279 lies entirely within the slop zones of the right appliance system 252. Since it does not, right appliance system 252 requires further analysis to find the remaining anchor points. Torque adjustment module 24 determines whether reference line 279 lies entirely within the slop zones of the left appliance system 254. In this example, the reference line 279 lies entirely within slop zone 228.

To phrase the actions of torque adjustment module 24 another way, torque adjustment module 24 determines whether the virtual representation of the archwire twist angle (line 279 in FIG. 6C) lies within the slop zone at each appliance position in the appliance system under analysis. If so, torque adjustment module has completed analysis of that appliance system. If not, the appliance system is further analyzed for additional anchor points.

Torque adjustment module next analyzes right appliance system 252 for additional anchor points. If the current reference line 279 lies entirely within all slop zones of the right appliance system 252, then torque adjustment module may determine that there are no other anchor points within the right appliance system 252. However, in this example, current reference line 279 does not lie entirely within all slop zones of right appliance system 252. Torque adjustment module therefore next analyzes the right appliance system 252 to identify additional anchor points.

To identify another anchor point in the right appliance system 252, torque adjustment module finds the torque angle having the maximum deviation from the current reference line. In this example, torque adjustment module identifies appliance position 215 as the position having the maximum deviation from reference line 279.

Figure 6D:
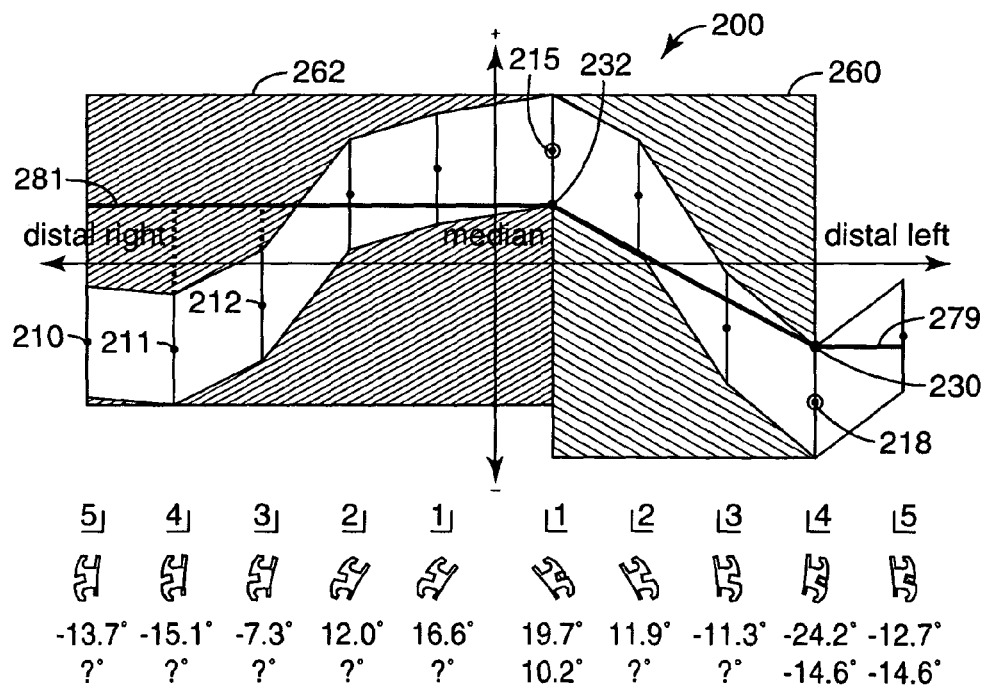

FIG. 6D is a diagram illustrating identifying appliance position 215 as the second anchor point. Position 215 is circled in FIG. 6D and all following figures to indicate that it is an anchor point. As described above with respect to first anchor point 230, torque adjustment module 24 next determines whether the archwire engages appliance position 215 at the positive or negative torque limit of slop zone 84. Torque adjustment module 24 identifies second anchor point 232 at the negative torque limit of the corresponding slop zone because second anchor point 232 lies above reference line 279.

Now that a new anchor point 232 has been identified, torque adjustment module 24 again divides appliance system 252 into right 262 and left 260 appliance systems. Again, torque adjustment module may first analyze the right appliance system 262. Torque adjustment module 24 then defines a new horizontal reference line 281 based on second anchor point 232. Torque adjustment module 24 determines whether a horizontal reference line 281 drawn from second anchor point 232 lies entirely within all slop zones in the current appliance system 262 (that is, slop zones 210-215). In this example, the current reference line 281 does not lie entirely within slop zones 210-215. Torque adjustment module 24 may also determine if second anchor point 232 is the left most appliance position of the root appliance system 250 (FIG. 6B).

FIG. 6D also illustrates selecting another anchor point in the current appliance system 262. Again, torque adjustment module 24 selects the appliance position having the torque angle with the maximum deviation from the current reference line. In this example, the current reference line is reference line 281 and the appliance position with the absolute maximum distance is appliance position 211.

Figure 6E:
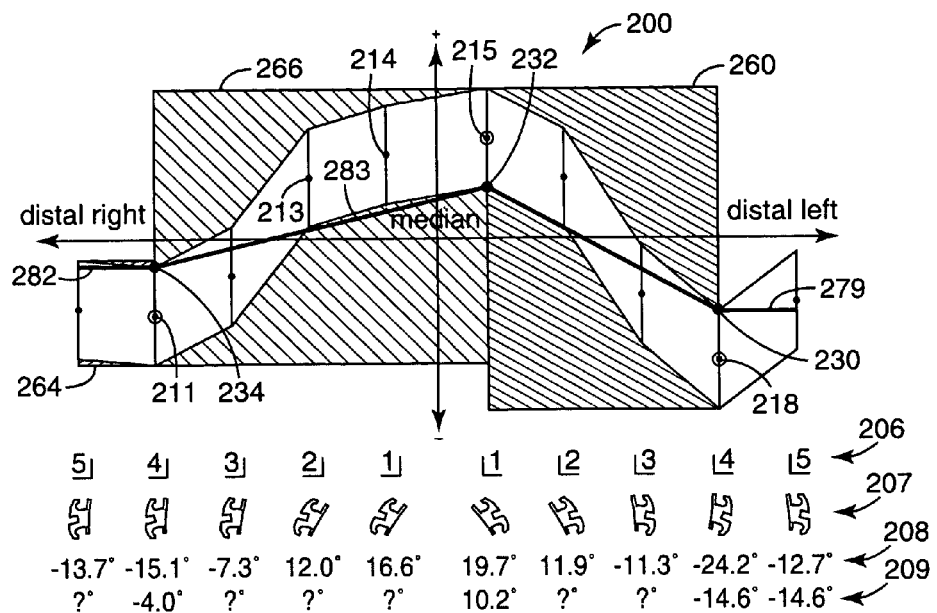

In FIG. 6E, appliance position 211 is circled to indicate that has an associated anchor point. Torque adjustment module 24 next determines if the archwire engages appliance position 211 at the positive or negative torque limit of the corresponding slop zone. In this example, torque adjustment module 24 identifies third anchor point 234 at the positive torque limit of slop because third anchor point 234 lies below reference line 281.

Because a new anchor point has been identified, torque adjustment module again subdivides the appliance system 262 (see FIG. 6E) into right 264 and left 266 appliance systems. Torque adjustment module 24 then analyzes the right appliance system 264 by defining a new horizontal reference line 282 based on third anchor point 234. Torque adjustment module 24 determines whether reference line 282 based on third anchor point 234 lies entirely within the slop zones of appliance system 264. In this example, the current reference line 282 does lie entirely within the slop zone of the current appliance system 264.

Torque adjustment control module analyzes the left appliance system 266 of the anchor point 234. Appliance system 266 is bound by two anchor points, 234 and 232. To locate anchor points within an appliance system bounded by two anchor points, torque adjustment module 24 may define a new reference line based on the two anchor points. Thus, in the example shown in FIG. 6E, torque adjustment module 24 defines reference line 283 as a line connecting anchor points 234 and 232. If this reference line 283 lies entirely within the slop zone of appliance system 266, then torque adjustment module 24 may determine that there are no additional anchor points within the appliance system 266. Torque adjustment module's 24 analysis of the appliance system 266 would therefore be finished.

In this example, however, reference line 283 does not lie entirely within the slop zone of appliance system 266. Therefore, torque adjustment module 24 locates a subset of appliance positions in the current appliance system where the current reference line does not pass through the slop zones. In this example, appliance positions 213 and 214 satisfy this definition of the subset of appliance positions. In one embodiment, torque adjustment module 24 may identify the appliance position from among this subset of appliance positions that has the maximum deviation from an appropriate reference line. In the example shown in FIG. 6E, appliance position 214 has the maximum deviation from reference line 283. Torque adjustment module 24 therefore identifies appliance position 214 as having an associated anchor point.

Figure 6F:
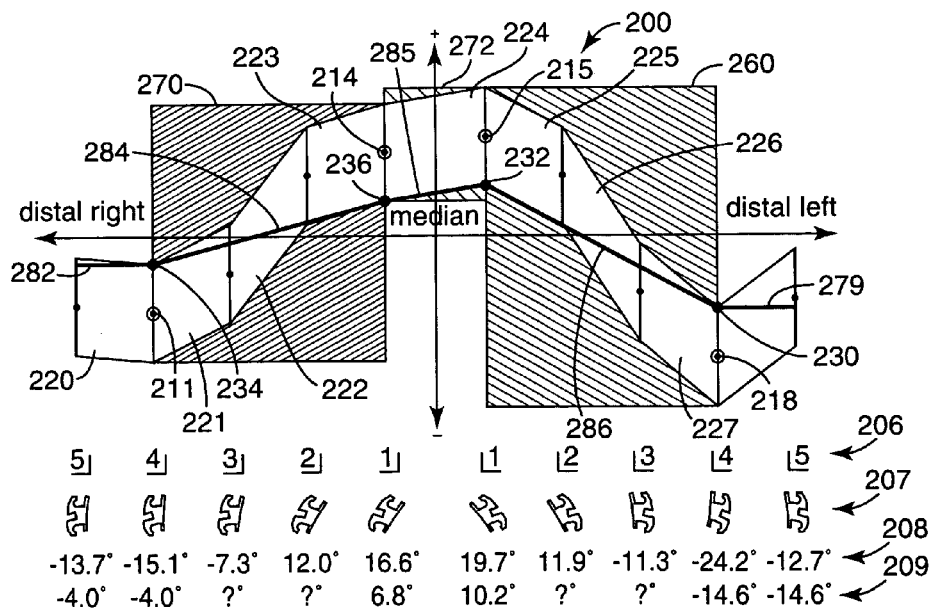

FIG. 6F shows appliance position 214 designated as having an associated anchor point 236. As described above, because anchor point 236 is above the current reference line 283 (FIG.

6E), torque adjustment module 24 sets the anchor point 236 at the negative torque limit of the corresponding slop zone.

Once anchor point 236 has been identified, torque adjustment module 24 further subdivides appliance system 266 into right 270 and left 272 appliance systems. Again, torque adjustment module 24 may first analyze the right appliance system 270, draw a reference line 284 between anchor points 234 and 236, and determine whether the reference line 284 lies entirely within the slop zones between anchor points 234 and 236. In this example, reference line 284 does lie entirely within slop zones 221, 222, and 223. Therefore, torque adjustment module 24 determines that there are no further anchor points in appliance system 270. Torque adjustment module's 24 analysis of appliance system 270 is therefore finished.

Next, torque adjustment module 24 looks at the left appliance system 272 for anchor point 236. In this example, the adjacent appliance position 215 is also identified as having an anchor point 232, so torque adjustment module determines that there are no further anchor points in appliance system 272. Torque adjustment module's 24 analysis of appliance system 272 is therefore finished.

Now, torque adjustment module 24 examines the left appliance system 260 associated with anchor point 232. FIG. 6F illustrates this portion of the process. Again, torque adjustment module 24 generates a new reference line 286 between anchor points (in other words, couples) 230 and 232 bounding the current appliance system 260, and determines whether the current reference line 286 lies entirely within the slop zone of the current appliance system 260. In this example, the current reference line 286 does not lie entirely within slop zones 225, 226, and 227.

To identify the position of another anchor point within appliance system 260, torque adjustment module 24 locates a subset of appliance positions in the current appliance system where the corresponding reference line does not pass through the slop zones. In this example, only appliance position 216 satisfies this definition. Appliance position 216 (FIG. 6G) is therefore identified as having an associated anchor point. If, however, the subset of appliance positions had included more than one appliance positions, torque adjustment module 24 may identify the appliance position from among this subset of appliance positions with the maximum deviation from the current reference line. Torque adjustment module 24 would then identify that appliance position as having an associated anchor point.

Figure 6G:
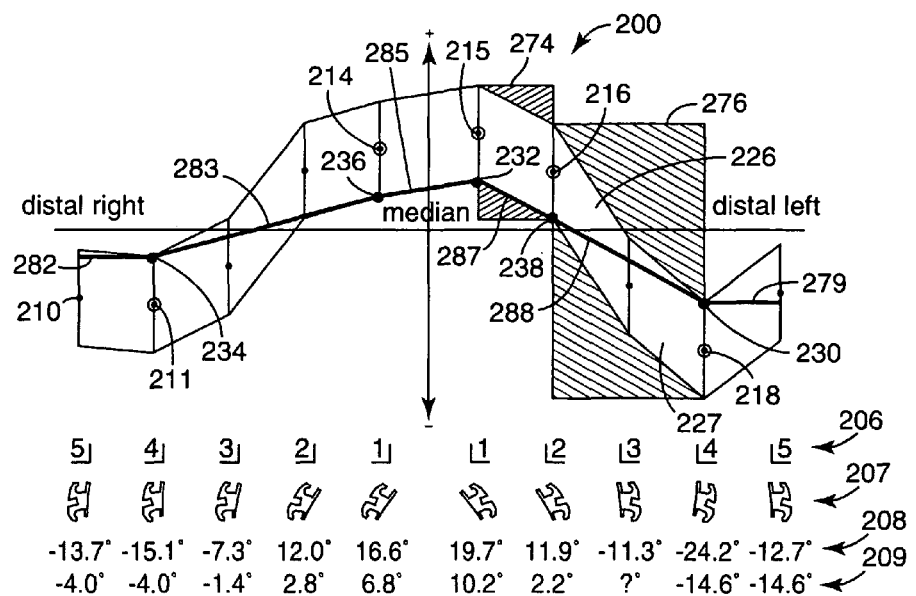

FIG. 6G shows appliance position 216 designated as an anchor point. Appliance position 216 is circled in FIG. 6G to indicate that it has an associated anchor point 238. Because anchor point 238 lies above reference line 286 (FIG. 6F), torque adjustment module 24 sets the negative torque limit associated with appliance position 216 as anchor point 238.

Now that a new anchor point 238 has been identified, torque adjustment module 24 further subdivides appliance system 260 into right 274 and left 276 appliance systems. Again, torque adjustment module 24 first looks at the right appliance system 274, draws a reference line 287 between anchor points 232 and 238, and determines whether the reference line 287 lies entirely within the slop zones between anchor points 232 and 238; that is, entirely within the slop zone of appliance system 274. In this example, anchor points 232 and 238 are adjacent. Therefore, torque adjustment module 24 determines that there are no further anchor points in appliance system 274. Torque adjustment module's 24 analysis of appliance system 274 is therefore finished.

Next, torque adjustment module looks to the left appliance system 276, draws a reference line 288 between anchor points 238 and 230, and determines whether reference line 288 lies entirely within the slop zones of appliance system 276. In this example, reference line 288 does lie entirely within slop zones 226 and 227. Torque adjustment module 24 therefore determines that there are no further anchor points in appliance system 276. Torque adjustment module is therefore finished analyzing appliance system 276.

Figure 6H:
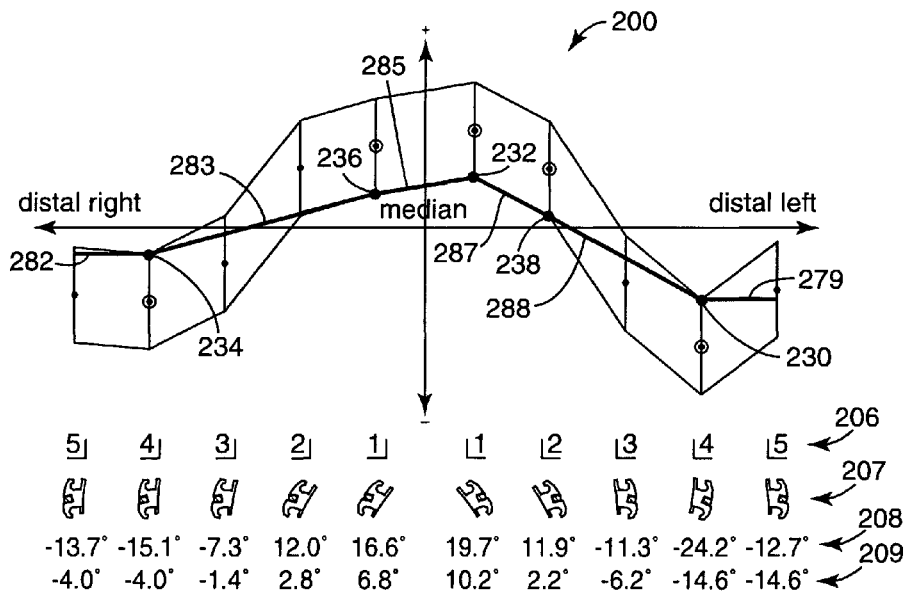

FIG. 6H shows the archwire-appliance system 200 after completion of one iteration of the above-described process. FIG. 6H shows anchor points 230, 232, 234, 236 and 238 and corresponding reference lines 282, 283, 285, 287, 288 and 279. These reference lines represent the archwire twist angle at every point along its length at a specific point in time during the course of orthodontic treatment. As the anchor points are determined during the course of the algorithm described above, the archwire twist angles (the numerical values of which are indicated generally by reference numeral 209 in the bottom row of FIG. 6H) at each appliance position along the length of the archwire are also determined. Torque adjustment module 24 then uses these archwire twist angles to compute a final occlusion adjusted for the effects of torque loss in the iterative adjustment process described above with respect to FIG. 5.

From FIG. 6H, it may also be seen that, in addition to determining the twist angle of the archwire at each appliance position, the twist angle of the archwire at any lengthwise position along the length of the archwire may also be determined. The twist angle of the archwire between appliance positions may be determined via the linear interpolation between twist angles of the archwire between appliance positions used to generate lines 282, 283, 285, 287, 288 and 279 which represent the twist angle of the archwire across the length of the entire archwire-appliance system. Thus, torque adjustment module 24 may find the twist angle at any lengthwise position along the archwire by reference to the resulting linear interpolation at the desired lengthwise position.

Figure 6I:
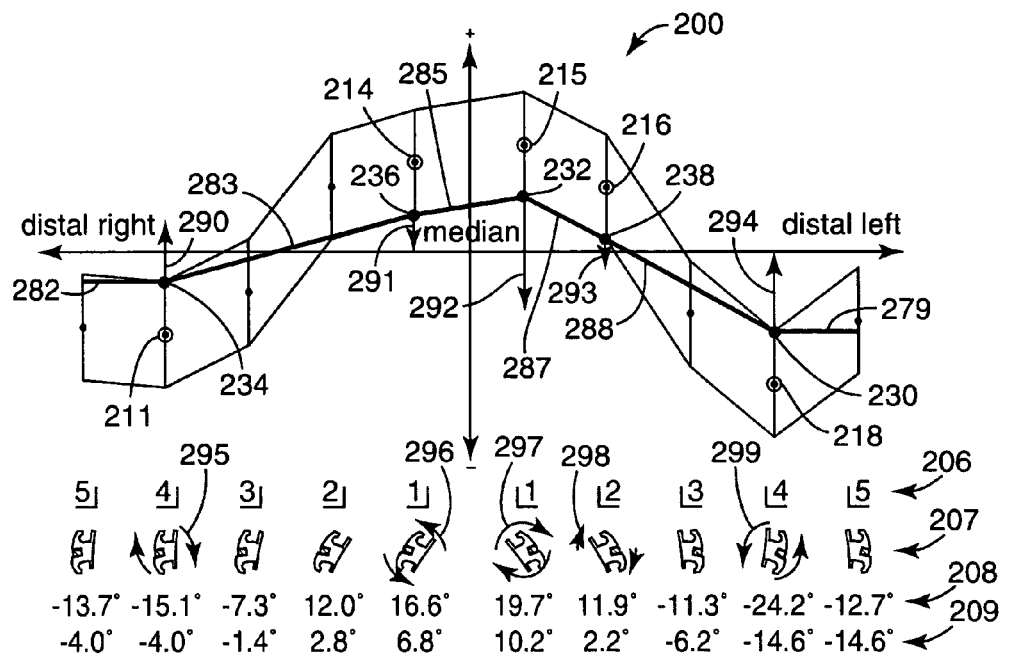

FIG. 6I illustrates how torque adjustment module 24 computes the resultant torque at anchor point for the example described above with respect to FIGS. 6A-6H. FIG. 6I shows linear torque vectors 290, 291, 292, 293, and 294 each corresponding to anchor points 234, 236, 232, 238 and 230, respectively. FIG. 6I also shows corresponding rotational torque vectors 295, 296, 297, 298 and 299 in the bracket cross-section graph 207. For illustrative purposes, the lengths of the linear torque vectors 290, 291, 292, 293, and 294 and the corresponding rotational torque vectors 295, 296, 297, 298 and 299 are shown somewhat to scale, corresponding to the magnitude of their respective vectors, and their directions have been drawn to correspond with their respective signs.

Figure 6J:
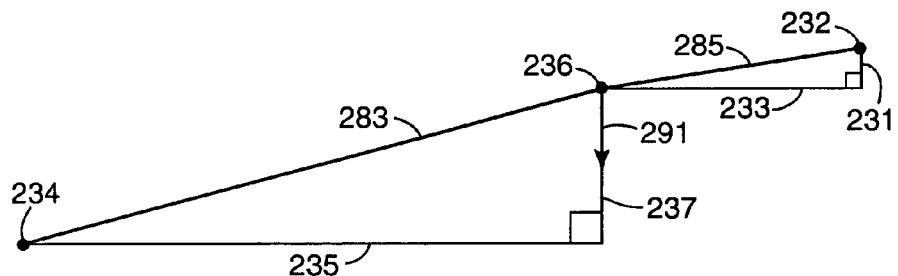

FIG. 6J shows an abstraction based on anchor points 234, 236 and 232 of the archwire-appliance system illustrated in FIG. 6I. However, it shall be understood that this abstraction is for illustrative purposes only, and that the principles described may apply to any group of anchor points. As discussed above, torque adjustment module 24 utilizes the following parameters:

$\phi_n$: total angle of twist at anchor point n,
$T_n$: resultant torque at anchor point n,
G: shear modulus of elasticity,
$I_p$: polar moment of inertia,
$d_n$: distance from the median line of anchor point n, and
$m_n$ is used to denote the slope of each line segment representing an archwire segment. A difference in $\phi$ may be referred to as a "delta phi" or "change in archwire twist angle", while a difference in d may be referred to as "L" or "length of archwire segment". "T" is similarly used to represent "resultant torque" at a given anchor point, which depends on the applied torque in the anchor points adjacent archwire segments. "T" also depends on "G" and "$I_p$", the modulus of elasticity of the archwire material and the polar moment of inertia of an archwire cross-section, respectively. It is also useful to note that the sign (+ or −) of T from this calculation determines the clockwise or counter-clockwise direction of the torque. Again, as discussed above, the torque in each archwire segment is directly proportional to the modulus of elasticity of the archwire material, polar moment of inertia of an archwire cross-section, and change in archwire twist angle, and inversely proportional to the length of the archwire segment.

In the example shown in FIG. 6J, to find the resultant torque at anchor point 236, anchor point 236 may be described with coordinates ($d_n$, $\phi_n$). Anchor point 234 may then be described with coordinates ($d_{n-1}$, $\phi_{n-1}$) and anchor point 232 may be described with coordinates ($d_{n+1}$, $\phi_{n+1}$). The length of line 235 may be given by ($d_n-d_{n-1}$), the length of line 233 may be given by ($d_{n+1}-d_n$), the length of line 237 may be given by ($\phi_n-\phi_{n-1}$), and the length of line 231 may be given by ($\phi_{n+1}-\phi_n$).

The slope of line 283 may be given by the following equation:

$$m_{n-1,n}=(\phi_n-\phi_{n-1})/(d_n-d_{n-1}).$$

Similarly, the slope of line 285 may be given by the following equation:

$$m_{n,n+1}=(\phi_{n+1}-\phi_n)/(d_{n+1}-d_n).$$

The resultant torque at anchor point 236 is then given by the equation:

$$T_n=GI_p(m_{n,n+1}-m_{n-1,n}).$$

FIGS. 7A-7D are flowcharts illustrating exemplary operation of torque adjustment module 24 executing on the client computing device to determine the twist angles of the archwire at each appliance position along the length of the archwire. Specifically, process 300 shown in FIGS. 7A-7D is used to find anchor points as described above with respect to FIGS. 6A-6H.

FIGS. 7A-7D shows the process for setting up a virtual representation of the dental arch and for making a first call to an analyze process to find the anchor points (300). A "root" appliance system may initially be defined as the archwire-appliance system for the entire dental arch (see, e.g., archwire-appliance system 250 of FIG. 6B). To initially define the root appliance system, torque adjustment module 24 defines a "Bracket Node" for each appliance position in the dental arch (302). As described above, the terms "right" and "left" as used herein are from the perspective of the patient, i.e., the patient's right and left, in the manner commonly used in the dental arts. The archwire-appliance system may be represented as a linked list, doubly linked list, stack, queue, heap, dictionary, tree, or any other suitable type of data structure.

The definition of each Bracket Node may include several variables, such as those shown in the following list.
  final int POSITIVE_ANCHORAGE=+1;
  final int NO_ANCHORAGE=0;
  final int NEGATIVE_ANCHORAGE=−1;
  final double pmDeltaPhi;
  double d;
  double slotPhi;
  double archwirePhi;
  int anchorage;
  BracketNode rightNeighbor;
  BracketNode leftNeighbor;

Note that the "final int" data type is an integer constant, the "final double" data type is a double-precision floating-point constant, the "int" data type is an integer variable, the "double" data type is a double-precision floating-point variable, and the BracketNode data type is a pointer or similar reference to another such BracketNode. It shall be understood that other data types may also be suitable to hold these values. For example, when using a linear array as a data structure, the variables might not be needed due to right and left neighbors being implicit in the organization of the data structure.

The variable "pm Delta Phi" represents the positive or negative (i.e., plus or minus) torque limits (½ of the total slop zone) for the Bracket Node. The pmDeltaPhi variable allows a different slop zone to be defined for each Bracket Node, if desired. The variable "d" represents the distance of the Bracket Node from the median line of the dental arch, where positive values are used to represent distances left of the median line, and negative values are used to represent distances right of the median line. The variable "slot Phi" represents the angle of the bracket slot in relation to the reference plane. The variable "archwire Phi" represents the twist angle of the archwire in relation to the reference plane.

The variable "anchorage" can attain values POSITIVE_ANCHORAGE when using the positive slop limit for the anchor point, NO_ANCHORAGE when the Bracket Node is not an anchor point, or NEGATIVE_ANCHORAGE when using the negative slop limit for the anchor point.

Each Bracket Node may also include an index, such as a pointer, to its immediately adjacent right neighbor and a pointer to its immediately adjacent left neighbor.

To further define the root appliance system, torque adjustment module 24 defines a variable, rightmost BN, as the rightmost bracket node of the root appliance system, and defines another variable, leftmost BN, as the leftmost bracket node of the root appliance system (304).

Torque adjustment module 24 defines the initial appliance system to be analyzed as the root appliance system (306). The defining information for the root appliance system, namely its parent appliance system (in this case, the root appliance system has no parent, so this variable is null), the rightmost BN and the leftmost BN are passed as parameters to an analyze module (308). Torque adjustment module 24 calls an analyze software module to find all of the anchor points in the root appliance system (308).

Figure 7A:
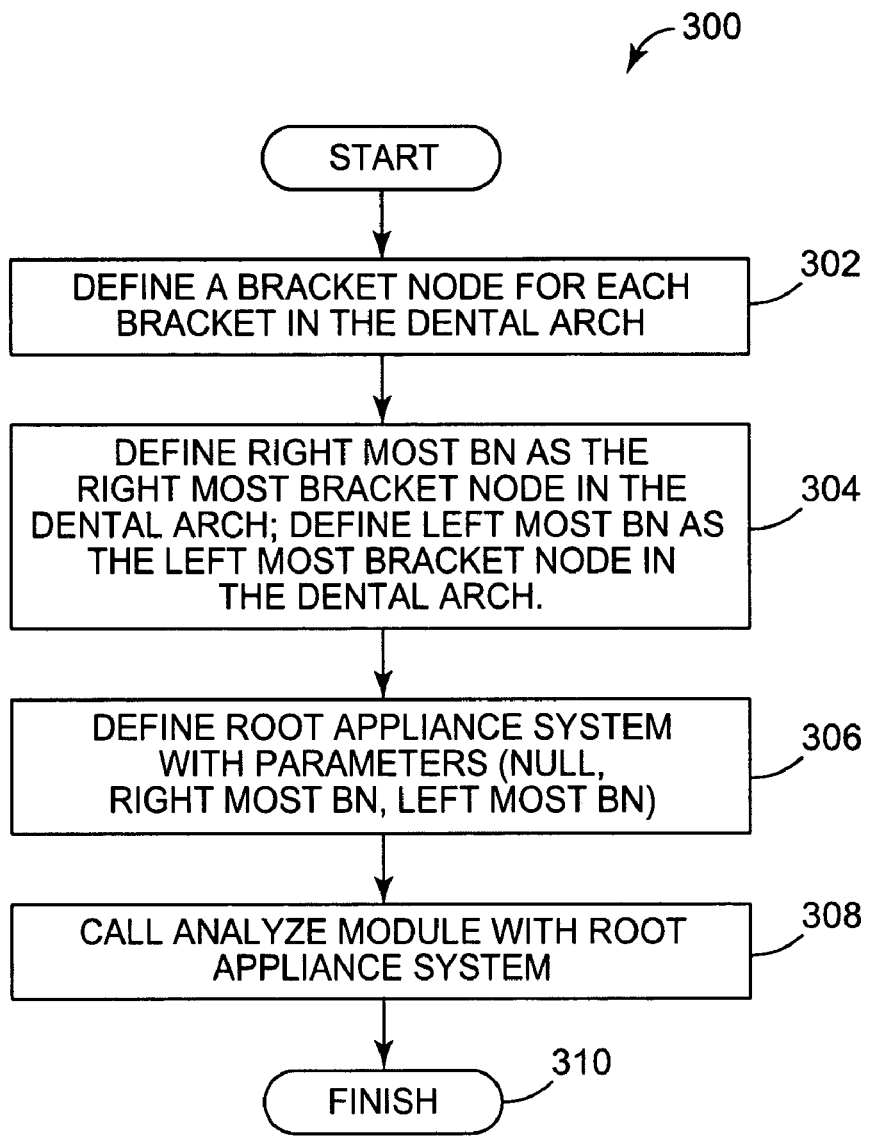
FIGS. 7A-7D are a flowchart illustrating exemplary operation of torque adjustment module executing on the client computing device to determine the twist angles of the archwire at each appliance position along the length of the archwire.
Figure 7B:
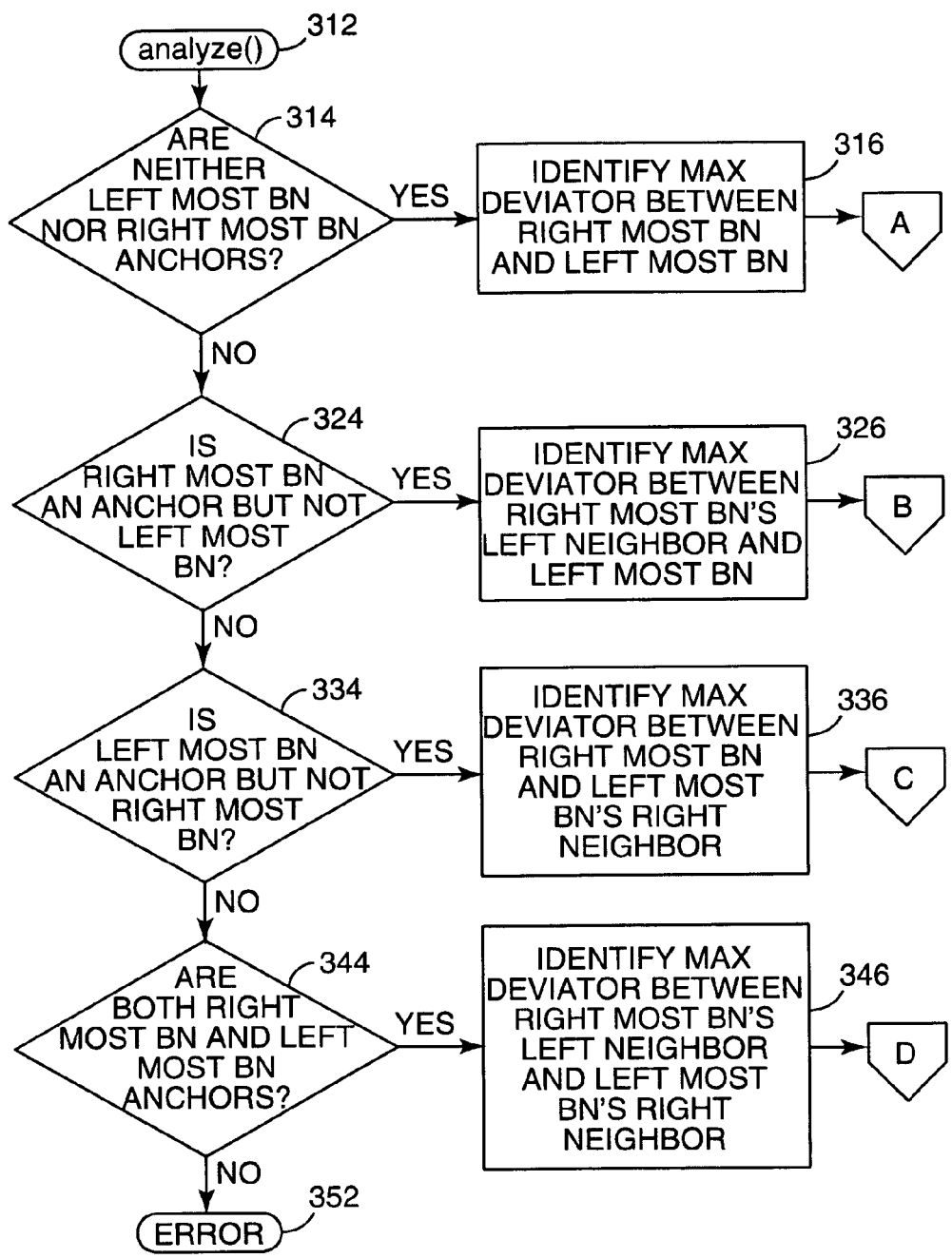

FIG. 7B shows a first portion of the analyze module (312). In the embodiment shown and described herein, there are four different types of appliance systems that may occur during analysis of the archwire-appliance system. A first type of appliance system may be one in which neither the leftmost bracket node nor the rightmost bracket nodes are anchors (314). A second type of appliance system may be one in which the right most BN is an anchor but the leftmost BN is not (324). A third type of appliance system may be one in which the leftmost BN is an anchor but the rightmost BN is not (334). A fourth type of appliance system may be one in which both the rightmost BN and the leftmost BN are anchors (344).

For each of these situations (314, 324, 334 and 344) torque loss control module 24 identifies the maximum deviator between the relevant Bracket Nodes (316, 326, 336 and 346). For example, for the first situation where neither the leftmost BN nor the rightmost BN are anchors (314), torque adjustment module 24 identifies the maximum deviator between and including the right most BN and the left most BN (316). This corresponds, for example, to the situation shown in FIG. 6B where no anchor points have yet been identified.

For the second situation where the rightmost BN is an anchor but the leftmost BN is not (324), torque adjustment module 24 identifies the maximum deviator between and including the right most BN's left neighbor and the left most BN (326). This corresponds, for example, to the situation shown in FIG. 6C, appliance system 254, where anchor point 218 is the rightmost BN and Bracket Node 219 is the leftmost BN (although in the example of FIG. 6C, there is no maximum deviator in appliance system 254)

For the third situation where the leftmost BN is an anchor but the rightmost BN is not (334), torque adjustment module 24 identifies the maximum deviator between and including the right most BN and the left most BN's right neighbor (336). This corresponds, for example, to the situation shown in FIG. 6C, appliance system 252, where anchor point 218 is the leftmost BN and Bracket Node 210 is the rightmost BN.

For the fourth situation where both the rightmost BN and the leftmost BN are anchors (344), torque adjustment module 24 identifies the maximum deviator between and including the right most BN's left neighbor and the left most BN's right neighbor (346). This corresponds, for example, to the situation shown in FIG. 6F, appliance system 260, where anchor point 218 is the leftmost BN and anchor point 215 is the right most BN.

Figure 7C:
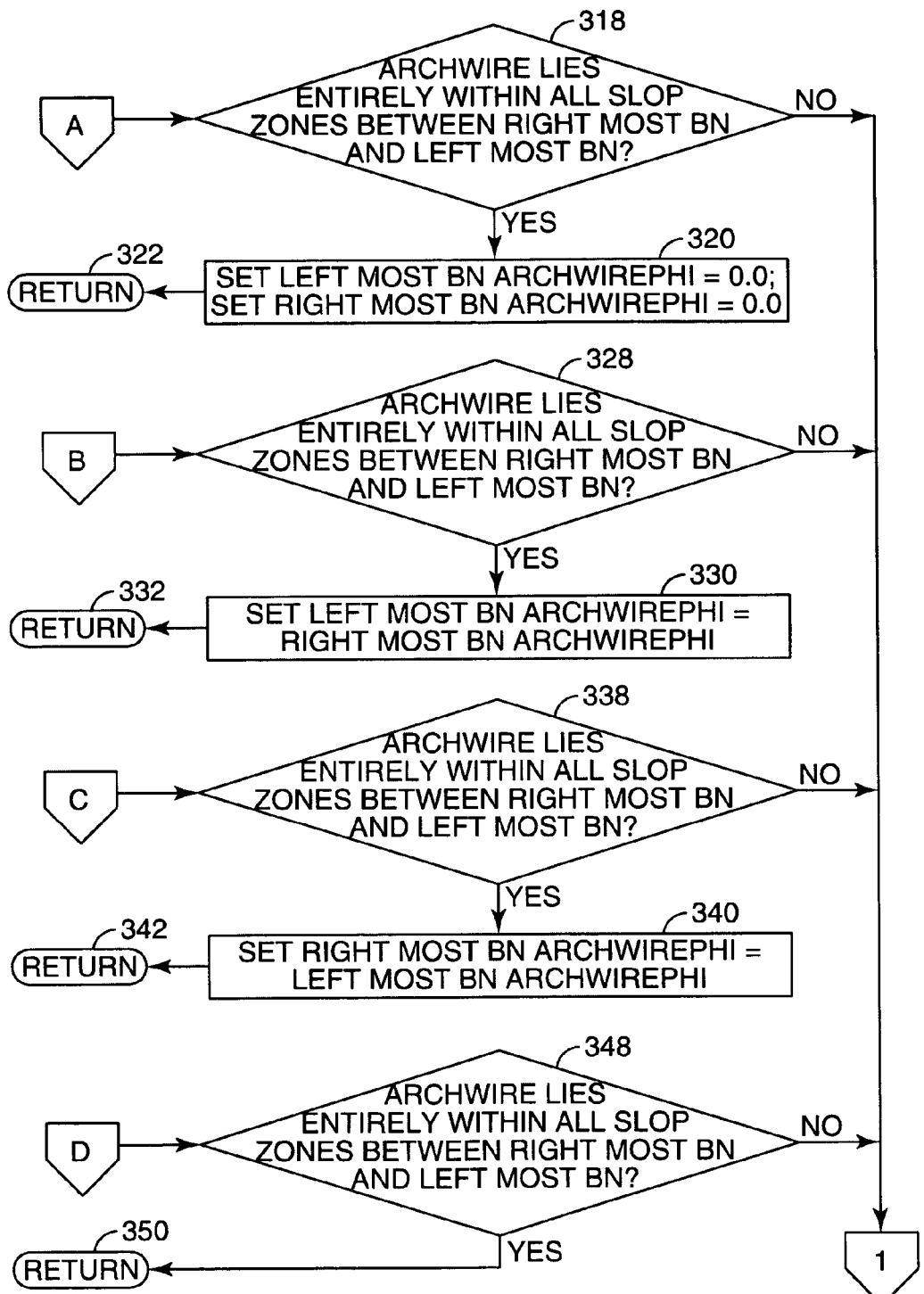

Once the maximum deviator has been identified (316, 326, 336, 346), torque adjustment module 24 determines whether the virtual representation of the archwire twist angle lies entirely within all slop zones between the right most BN and the left most BN as shown in FIG. 7C (318, 328, 338, and 348). For example, for the first situation where the neither the right most BN nor the left most BN are anchors, torque adjustment module 24 determines whether the reference line lies entirely within all of the slop zones in the current appliance system (that is, whether the maximum deviator lies within the slop zone of its bracket at every bracket node in that appliance system). This corresponds, for example, to FIG. 6B and line 202, in which case the reference line does not lie entirely within all of the slop zones.

For the second or third situation where only one of the right most BN or the left most BN are anchors, torque adjustment module 24 determines whether reference line lies entirely within all of the slop zones (i.e., whether the maximum deviator lies within the slop zones of each bracket in that appliance system). This situation corresponds, for example, to FIG. 6D and line 281, where only leftmost BN 215 is an anchor point, in which case the reference line does not lie entirely within all of the slop zones.

For the fourth situation where both the right most BN and the left most BN are anchors, torque adjustment module 24 determines whether reference line (i.e., the virtual representation of the archwire twist angle) lies within the slop zones at every bracket node in that appliance system. This situation corresponds, for example to FIG. 6G and line 288, where both right most BN 216 and left most BN 218 are anchor points, in which case the reference line does lie entirely within all of the slop zones of that appliance system.

If the virtual representation of the archwire twist angle (i.e., the reference line) does lie entirely within all slop zones at every bracket node in the appliance system (318, 328, 338, 348), torque adjustment module 24 sets the archwire twist angle (archwire Phi as defined above) to an appropriate value (320, 330, 340). For example, for the first situation where neither the left most BN nor the right most BN are anchor points, and the archwire lies entirely within the slop zones, torque adjustment module 24 sets left most BN archwire twist angle to zero and also sets the right most BN archwire twist angle to zero.

For the second situation where the right most BN is an anchor point, the left most BN is not an anchor point and the archwire twist angle lies entirely within the slop zones, torque adjustment module 24 sets the archwire twist angle of the left most BN to equal the archwire twist angle of the right most BN (330). Similarly, for the third situation where the left most BN is an anchor point, the right most BN is not and the archwire twist angle lies entirely within the slop zones, torque adjustment module 24 sets the archwire twist angle of the right most BN to equal the archwire twist angle of the left most BN (330).

For the fourth situation, where both the right most BN and the left most BN are both anchor points, the archwire twist angles are not adjusted.

After the archwire twist angles of the right most BN and the left most BN are set (320, 330, 340), torque adjustment module 24 returns (322, 332, 342, 352) back to the point in the algorithm from it called the analyze process. For example, if the current level was called from FIG. 7A (308), the process would return back to that point. Similarly, if the current level was called from FIG. 7D (380, 386), torque adjustment module would return back to that point when analysis of that appliance system is completed. These latter two calling points exemplify the recursive nature of the embodiment illustrated in FIGS. 7A-7D.

Figure 7D:
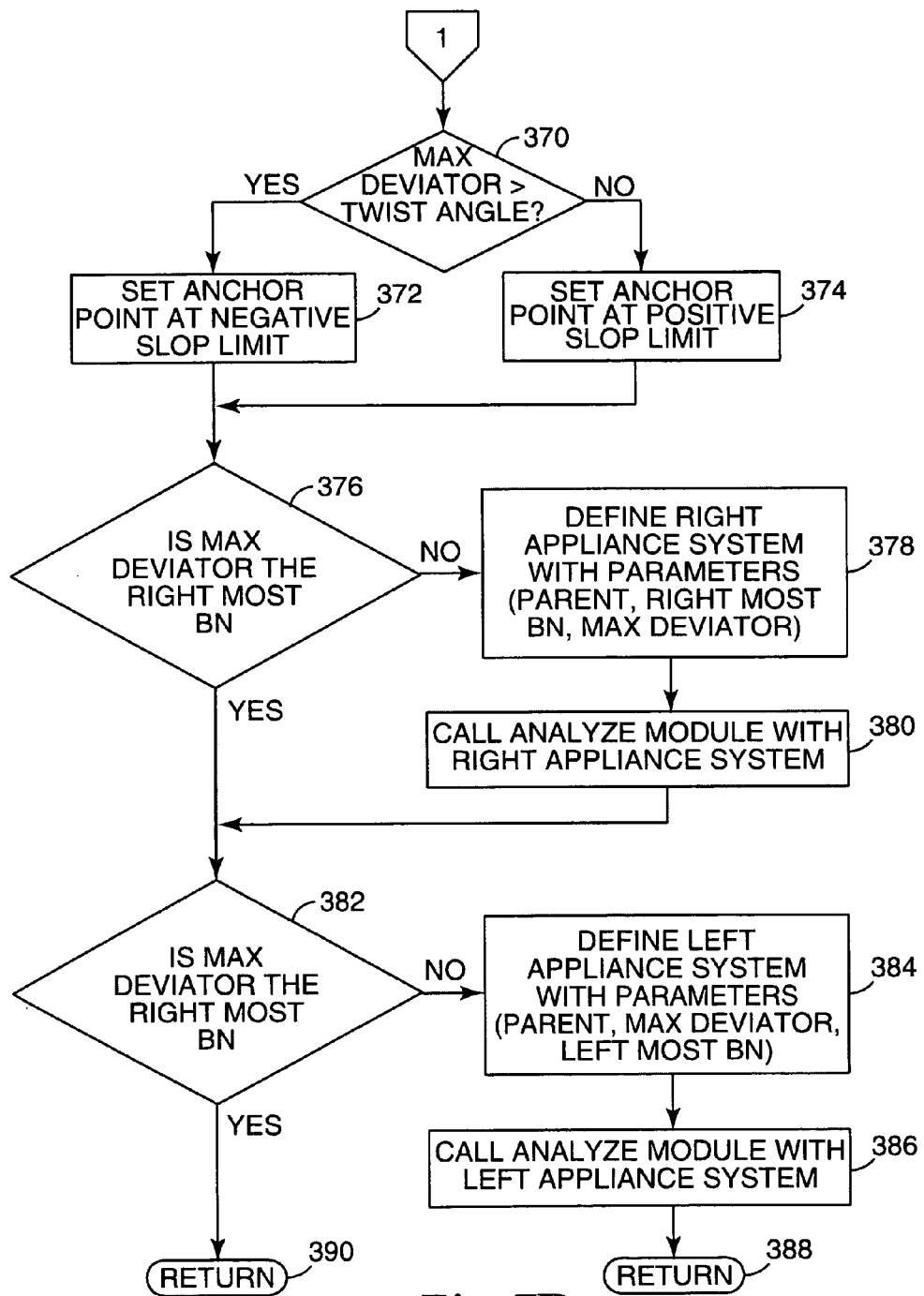

If, on the other hand, the virtual representation of the archwire twist angle does not lie entirely within all of the relevant slop zones (318, 328, 338, 348) the analyze process continues as shown in FIG. 7D. Torque control module 24 determines whether the max deviator is greater than the twist angle of the archwire (370). If so, torque adjustment module 24 sets the anchor point at the negative slop limit for that Bracket Node (372). This corresponds, for example, to FIG. 6D, where the anchor point 232 is set at the negative torque limit for Bracket Node 215. If the max deviator is less than the twist angle of the archwire (370), torque adjustment module 24 sets the anchor point at the positive slop limit for that Bracket Node (374). This corresponds, for example, to FIG. 6C, where anchor point 230 is set at the positive slop limit for Bracket Node 218.

Torque adjustment module 24 determines whether the maximum deviator is the right most Bracket Node in the root appliance system (376). If so, then the process has analyzed the dental arch to its distal right most point. An example of this is shown in FIG. 6E by appliance system 264. If the maximum deviator is not the right most Bracket node in the root appliance system (376), torque adjustment module 24 defines a new appliance system as the right appliance system with the parameters of the parent appliance system, the right most BN, and the maximum deviator as the left most BN (378). Torque adjustment module 24 then recursively calls the analyze module to operate on the right appliance system (380).

Once analysis of the right appliance system has been completed, or if the maximum deviator was not the right most Bracket Node in the root appliance system (376) torque adjustment module 24 determines whether the maximum deviator is the left most Bracket Node in the root appliance system (382). If so, then the process has analyzed the dental arch to its distal left most point. If the maximum deviator is not the left most Bracket Node in the root appliance system, torque adjustment module 24 defines a new appliance system as the left appliance system with the parameters of the parent appliance system, the maximum deviator as the right most BN, and the left most BN (384). Torque adjustment module 24 then recursively calls the analyze module to operate on the left appliance system (386).

When torque adjustment module 24 completes the analysis of the left appliance system, or if the maximum deviator was the left most bracket node in the root appliance system (382) torque adjustment module 24 returns (388 or 390, respectively) to the point in the analyze process at which it was called (388 or 390, respectively). Torque adjustment module 24 continues to recursively analyze the dental arch in this manner until all of the anchor points across the entire dental arch have been identified.

The process shown in FIG. 7D (376, 378, 380, 382, 384, 386) corresponds to dividing a parent appliance system into right and left appliance systems, and then analyzing the right and left appliance systems. An example of this can be seen in FIGS. 6E and 6F, where appliance system 266 (i.e., the "parent" appliance system in this case) is divided into right appliance system 270 and left appliance system 272. The parameters passed when calling the analyze process for the right appliance system 270 would include an index or pointer to the parent appliance system (appliance system 266), the right most BN (Bracket Node 211 in this case) and the maximum deviator would be passed as the left most BN (Bracket Node 214 in this case). Similarly, the parameters passed when calling the analyze process for the left appliance system 272 would include an index or pointer to the parent appliance system (appliance system 266 in this case, the maximum deviator as the right most BN (Bracket Node 214 in this case) and the left most BN (Bracket Node 215 in this case).

In the analyze process shown in FIG. 7D, the appliance systems are examined until it is found that the archwire twist angle lies entirely within the slop zones of every bracket node in each appliance system. At that point, torque adjustment module 24 has found all of the anchor points in the dental arch. The process then returns back to the highest level of the recursive algorithm, i.e., the root appliance system (308 in FIG. 7A) and the process is finished (310).

Although the iterative adjustment process has been described with respect to a specific sequence of events, it shall be understood that the invention is not limited to the determination of anchor points, terminal points, appliance systems, reference lines or any other variable identified in the iterative adjustment process in any certain order. Rather, the embodiment described above with respect to FIGS. 6A-6H and FIGS. 7A-7D is but one example of many variations with which the anchor points of an archwire-appliance system may be determined. For example, although the process described above referred to analyzing the right appliance system and then the left appliance system, another embodiment may analyze the left appliance system and then the right. As another example, although the process described above is a recursive process, other embodiments need not use recursion, but may instead use other methods of finding the anchor points. For example, detailed procedural methods that do not use recursion could be used to analyze the archwire-appliance system. Similarly, the recursive process may be implemented using a recursive programming language or may be implemented using stacks to save the states each time a new appliance system to be analyzed is identified. In addition, other factors may be varied within the iterative adjustment process without departing from the scope of the present invention. It shall be understood, therefore, that the iterative adjustment process described herein may be varied, and that the invention is not limited in this respect.

One or more of the techniques described herein may be partially or wholly executed in software. For example, a computer-readable medium may store or otherwise comprise computer-readable instructions, i.e., program code that can be executed by a processor to carry out one or more of the techniques described above. For example, the computer readable medium may comprise random access memory (RAM), read-only memory (ROM), non-volatile random access memory (NVRAM), electrically erasable programmable read-only memory (EEPROM), flash memory, magnetic or optical media, or the like. The instructions and the media are not necessarily associated with any particular computer or other apparatus, but may be carried out by various general-purpose or specialized machines. The instructions may be distributed among two or more media and may be executed by two or more machines. The machines may be coupled to one another directly, or may be coupled through a network, such as a local access network (LAN), or a global network such as the Internet.

Other variations of the iterative adjustment process shown in FIGS. 6A-6H and 7A-D are also possible. For example, the process described herein breaks an appliance system into left and right appliance systems based on a maximum deviator. However, in another embodiment, an appliance system could be split into a left, middle, and right appliance system based on a maximum deviator and a minimum deviator. Those of skill in the art will readily see that there are many ways to analyze the archwire-appliance system without departing from the scope of the present invention.

FIGS. 8A-8D are display diagrams of an exemplary user interface 400 presented by the modeling software 20. In the illustrated embodiment, user interface 400 includes a menu input area 406 by which a user, e.g., practitioner 8, accesses an electronic prescription for patient 6. User interface 400 includes display area 408 for presenting the 3D rendered representation of the teeth of patient 6. User interface 400 provides selection mechanism 412 by which practitioner 8 can selectively enable and disable the rendering and display of any of several different views of the patient's dental arch within the display area 408.

The iterative adjustment process described above may be used to animate third-order rotations of teeth from initial malocclusion to a computed final occlusion adjusted for torque loss in a 3D virtual world. In this example, display area 408 presents an animation showing the iterative adjustment process from malocclusion to a final occlusion adjusted for the effects of torque loss. FIGS. 8A-8D illustrate selected time frames during the iterative adjustment process, from the initial malocclusion (FIG. 8A), two time frames taken during the iterative adjustment process (FIGS. 8B and 8C) and a representation of a final occlusion adjusted for the effects of torque loss (FIG. 8D).

Figure 8A:
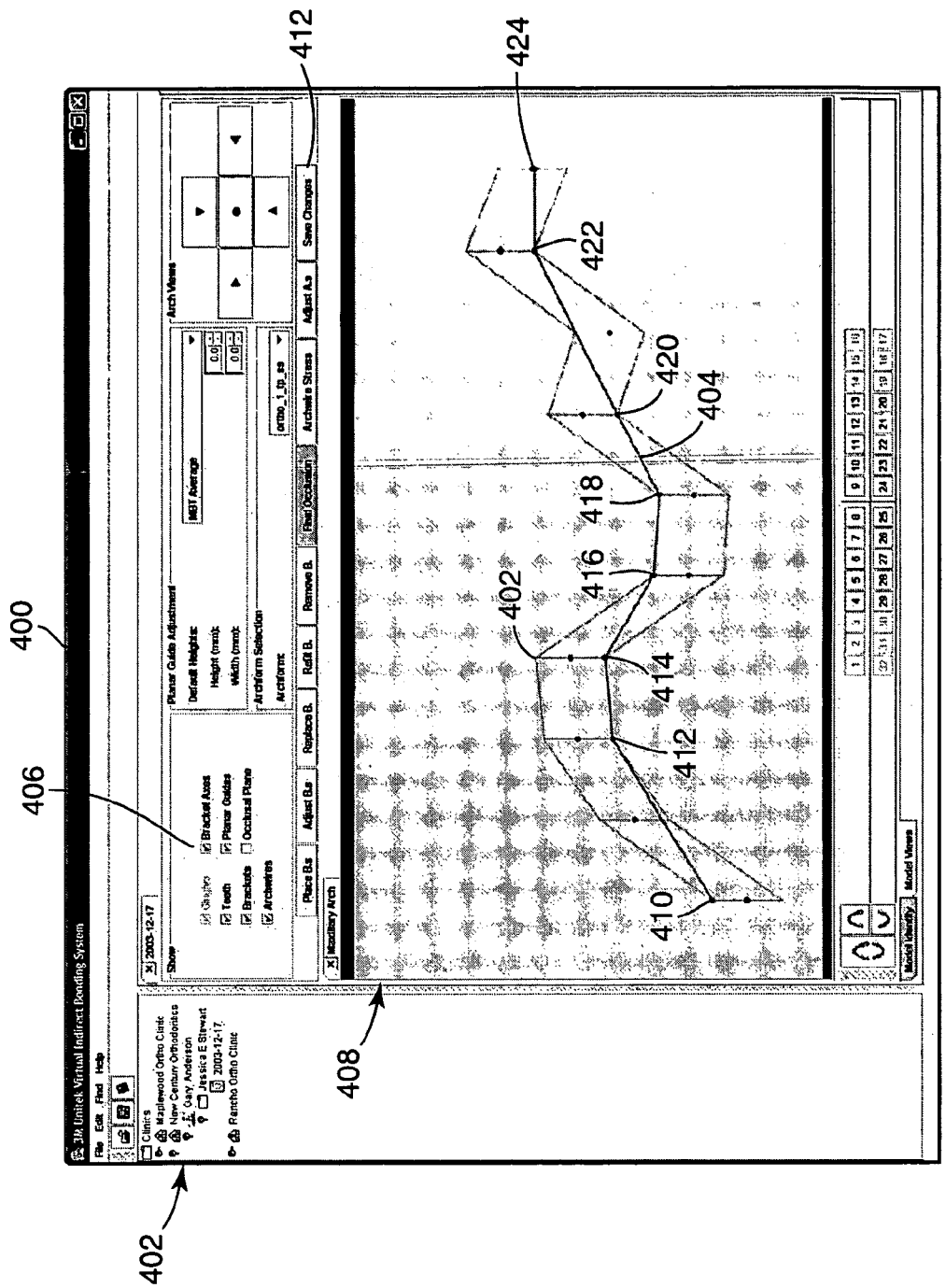
FIGS. 8A-8D are display diagrams of an exemplary user interface presented by the modeling software.

Beginning with FIG. 8A, a representation of a set of brackets of FIG. 8A generally illustrates a representation of an example archwire-appliance system 402 for a dental arch in malocclusion. The example archwire-appliance system 402 shown in FIG. 8A corresponds to a patient's dental arch at the beginning of a course of orthodontic treatment. Archwire 404 is shown engaging the brackets at anchor points 410, 412, 414, 416, 418, 420, and 422.

Figure 8B:
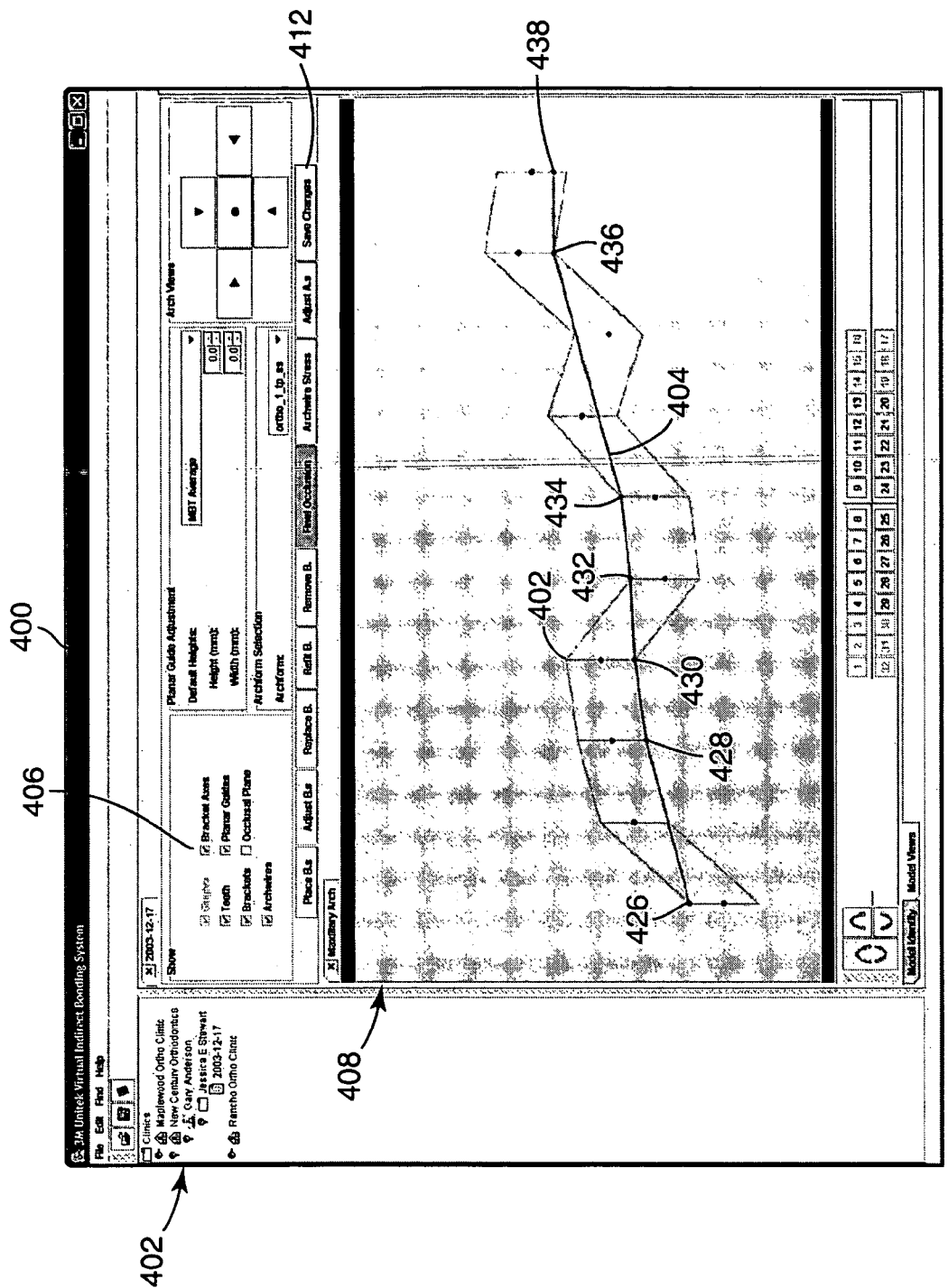
Figure 8C:
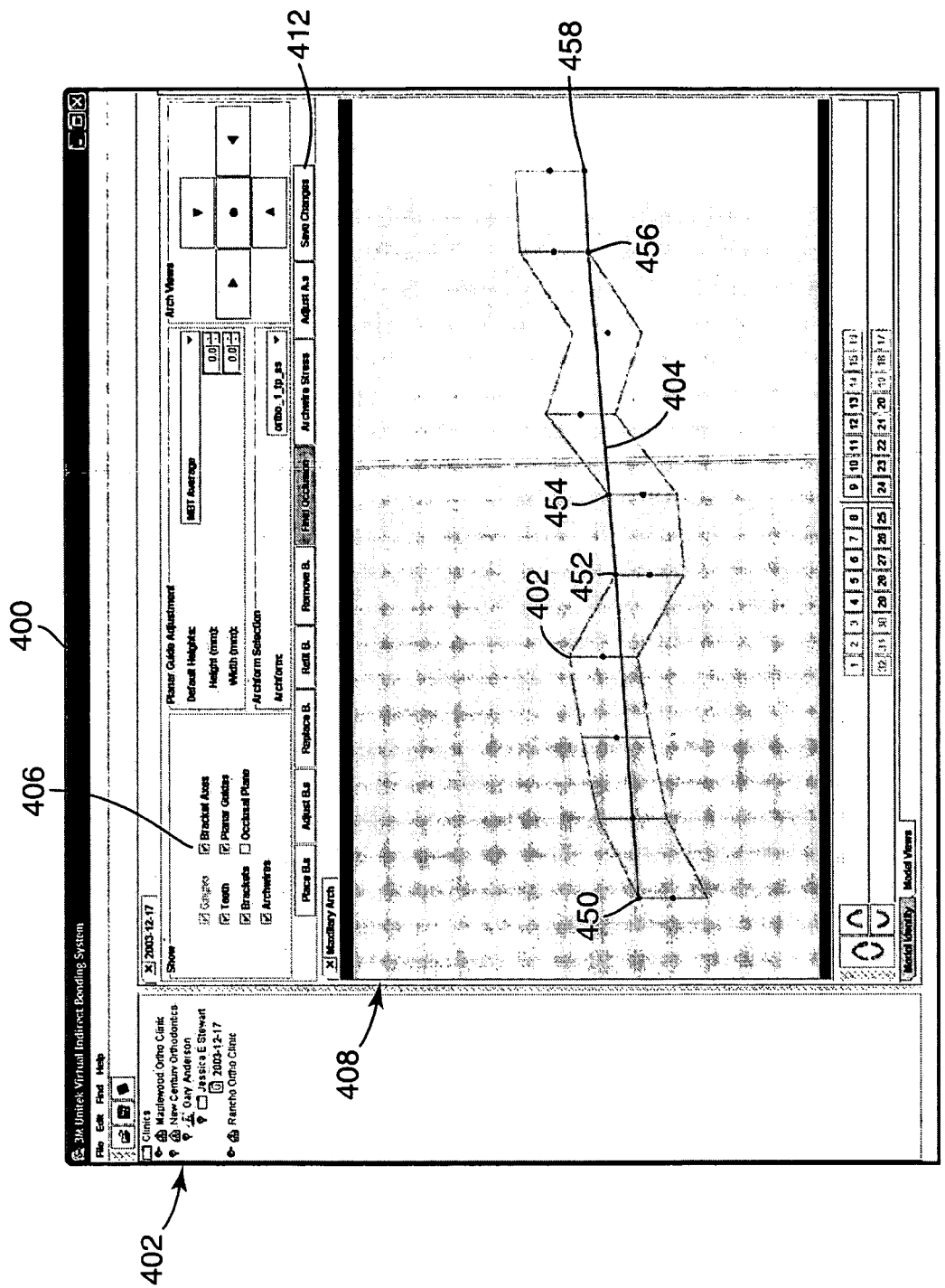
Figure 8D:
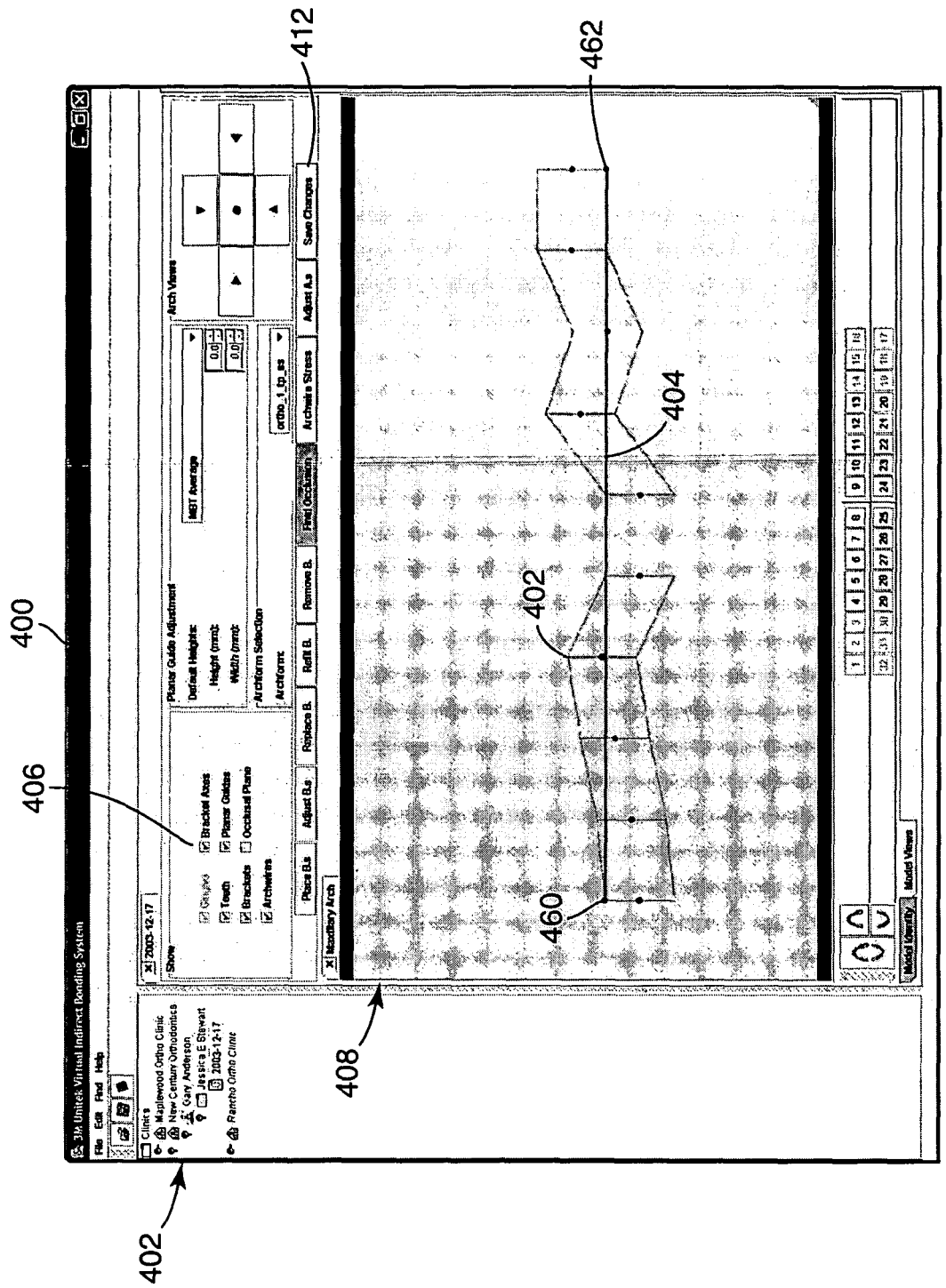

After some number of iterations of the iterative adjustment process, the example archwire-appliance system 402 may look like that shown in FIG. 8B. Here, archwire 404 is shown engaging the brackets at anchor points 426, 428, 432, 434 and 436. After some further iterations of the iterative adjustment process, the example archwire-appliance system 402 may look like that shown in FIG. 8C. Here, archwire 404 is shown engaging the brackets at anchor points 450, 452, 454, 456 and 458.

Finally, FIG. 8D illustrates a representation of the archwire-appliance system 402 in final occlusion that has taken the effects of torque loss into account.

FIGS. 8A-8D simulate the relaxation of archwire 404 over the course of orthodontic treatment. The twist angle of archwire 404 approaches zero during the course of the iterative adjustment process. This causes the representation of archwire 404 shown in FIGS. 8A-8D to "flatten out" or become horizontal over time. Final occlusion is reached when the twist angle of archwire 404 is approximately equal to zero, i.e., the line segments representing archwire 404 have approximately zero slope.

Figure 9A:
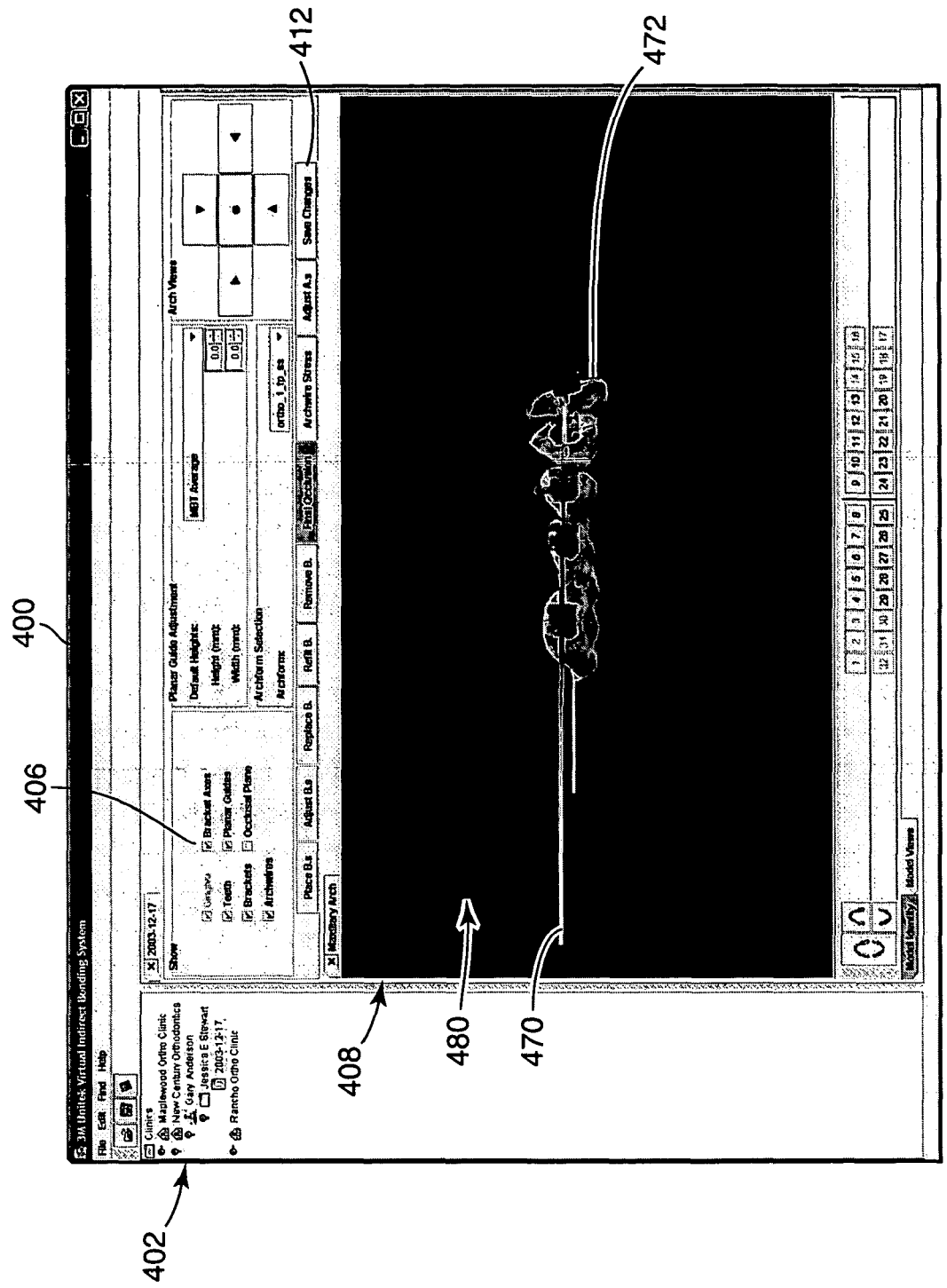
FIGS. 9A-9B are display diagrams of an exemplary user interface presented by the modeling software.
Figure 9B:
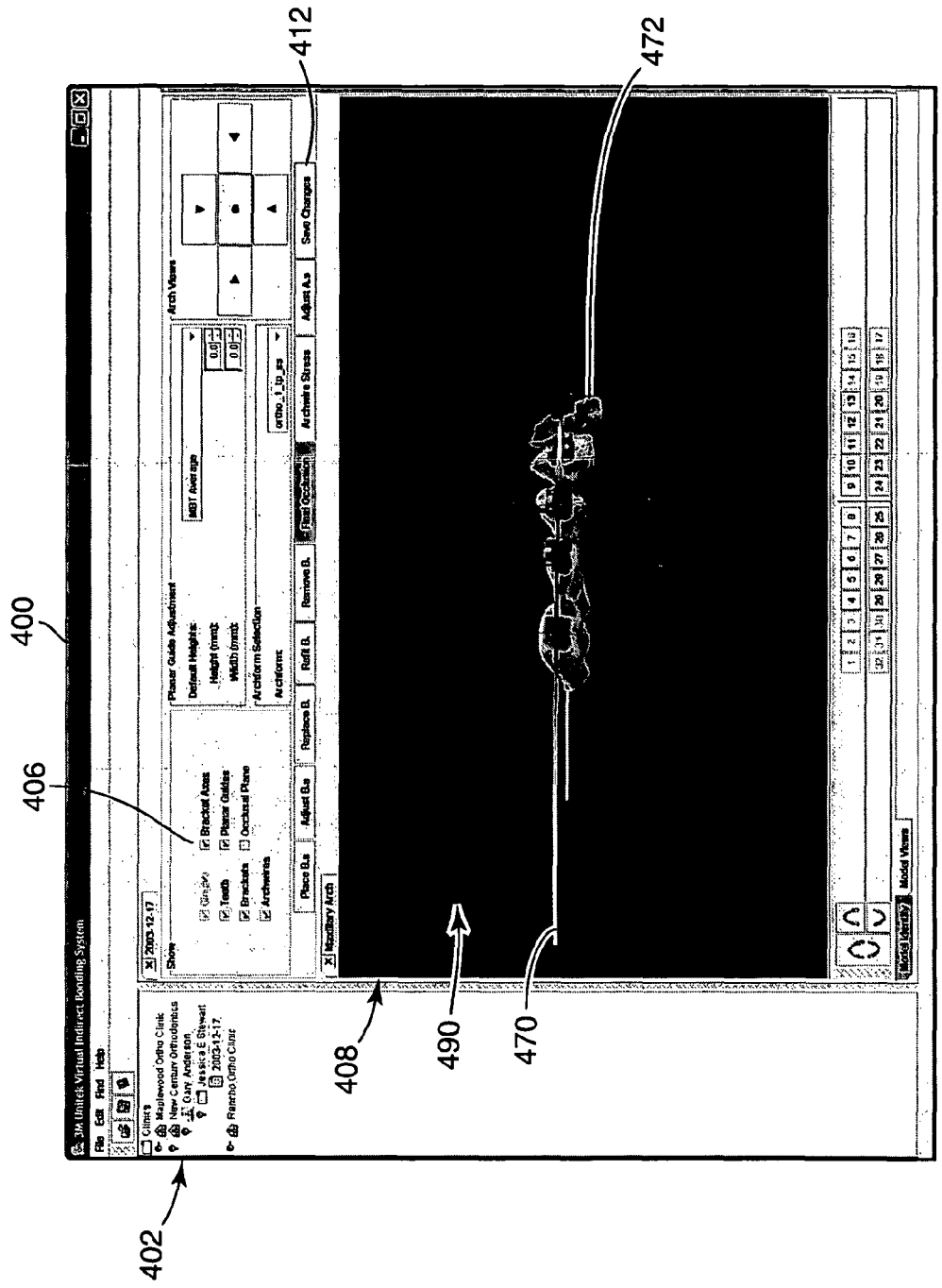

FIGS. 9A-9B are display diagrams of an exemplary user interface 400 presented by the modeling software 20. FIGS. 9A and 9B illustrates an exemplary embodiment in which modeling software 20 places display area 408 into a torque loss view mode. The example display area 408 of FIG. 9A illustrates an intended final occlusion 480 assuming full engagement of the archwire 470 with all of the orthodontic appliances during the course of orthodontic treatment. When in torque loss view mode, user interface 400 allows a practitioner to view a model of the intended final occlusion 480, which may include the archwire, brackets, teeth, and/or gingiva, such as that shown in FIG. 9A and a model of the computed final occlusion 490 derived from modeling engagement of the archwire with the slots of the orthodontic appliances throughout a course of orthodontic treatment with the proposed prescription, such as that shown in FIG. 9B. The practitioner may then view the modeled intended 480 and computed 490 final occlusions to decide whether the proposed orthodontic prescription will produce the desired outcome once the effects of torque losses on the archwire-appliance system are taken into account.

Comparison of FIGS. 9A and 9B, for example, reveals that the maxillary right central incisor 472 in the computed final occlusion 490 (FIG. 9B) has a greater angle of inclination with respect to the vertical axis than does the same maxillary right central incisor 472 in the intended final occlusion 480 (FIG. 9A) which does not take the effects of torque loss on the archwire-appliance system into account. A practitioner assessing these views may then make a decision as to whether the proposed orthodontic prescription will produce an acceptable final occlusion after being able to visualize the effects that torque loss on the archwire-appliance system will have on the final result. Further, a practitioner may consequently select brackets that embody different inherent torque angles in their geometries or place brackets at different positions or orientations on the teeth to compensate for the predicted effects of torque loss.

In addition to displaying the initial malocclusion, intended final occlusion and/or computed final occlusion, the system may also display computed occlusions at discrete points in time throughout the course of treatment with the proposed prescription. These can be generated based on the twist angles of the archwires and corresponding appliance and tooth positions at these discrete points in time, such as those illustrated in FIGS. 8A-8D. The 3D representation of the computed occlusions at discrete points in time may include the archwire rendered in varying colors corresponding with the torsional stress in each archwire segment. Different colors could be assigned to correspond to different levels of torsional stress. This allows the practitioner to see not only the positions of the teeth, the appliances and the archwire at any given time, but also to view the torsional stress in the archwire, which is really not visible by viewing a pictorial representation of the archwire alone.

In addition, the 3D representation of the computed occlusions at discrete points in time may also include the appliances rendered in varying colors corresponding to the resultant torque on each appliance. Similarly, appliances that engage the archwire and that therefore have associated anchor points may be distinguished from appliances that do not engage the archwire by a difference in appearance.

Color coding of the archwire segments and/or the appliances allows the practitioner to view the teeth, archwire, appliances, torsional stress on the archwire, and the resultant torque on each appliance at discrete points in time to be viewed on a single 3D representation.

If the archwire is presumed to have a uniform cross section along its length, then the torsional stress in each archwire segment between couples is constant. This is represented in the Figures as line segments of constant slope between anchor points. Thus, in one embodiment, each segment of the archwire between anchor points may be displayed as a single color between. When displaying a 3D animation from initial occlusion to final occlusion throughout the course of treatment with the proposed prescription, each archwire segment may have a color, and each appliance may have a color, and those the colors will change over time as the animation progresses. A user can thus visualize which archwire segments and/or appliances are under high stress and which are under low stress, etc. When the animation is complete or when the predicted final occlusion is computed, any color remaining in the archwire and/or in the appliances will indicate residual stresses on the archwire-appliances system that are insufficient to result in movement of the teeth.

The colors may be indicated in any of various ways. For example, the different colors may be assigned to different levels of torsional stress in the archwire and/or different levels of resultant torques applied to the appliances. A key indicating the assignments may be displayed to the user. Color may be varied by hue, saturation, brightness, chroma, lightness, shade, gray scale, opacity, transparency, turbidity, or by any other appropriate means of indicating a difference.

Various embodiments of the invention have been described. Nevertheless, it is understood that various modifications can be made without departing form the invention. These and other embodiments are within the scope of the following claims.

The invention claimed is:

1. A method comprising:
digitally representing a proposed orthodontic prescription that includes a plurality of orthodontic appliances each associated with a different one of a plurality of teeth in a dental arch and an archwire received in a slot of each of the orthodontic appliances; and
computing a predicted final occlusion for the dental arch based on modeling effects of torque loss experienced by digital representations of the archwire and the orthodontic appliances throughout a course of treatment with the proposed orthodontic prescription within a three-dimensional (3D) modeling environment.

2. The method of claim 1, wherein the torque loss includes at least one of incomplete archwire expression and less than full engagement of the archwire in the slots of each of the orthodontic appliances.

3. The method of claim 1, wherein computing a predicted final occlusion comprises determining a twist angle of the archwire at each appliance position along the archwire.

4. The method of claim 3, wherein determining a twist angle of the archwire comprises iteratively determining a twist angle of the archwire at each appliance position along the archwire.

5. The method of claim 3, wherein computing a final occlusion comprises determining a twist angle or the archwire at any lengthwise position along the archwire.

6. The method of claim 5, wherein determining a twist angle of the archwire at any lengthwise position along the archwire comprises linearly interpolating between the twist angles of the archwire between appliance positions.

7. The method of claim 3, wherein determining a twist angle comprises:
determining a torque angle for each orthodontic appliance; and
determining positive and negative torque limits of the archwire for each orthodontic appliance.

8. The method of claim 5, wherein the torque angle for each orthodontic appliance is determined with respect to a reference occlusal plane.

9. The method of claim 3, wherein determining a twist angle comprises:
identifying anchor points along the archwire from among the appliance positions;
generating line segments between anchor points; and
determining the twist angle of the archwire based on the line segment associated with each appliance position.

10. The method of claim 9, wherein the generated line segments represent the twist angle of the archwire.

11. The method of claim 9, wherein identifying anchor points comprises:
identifying a maximum deviator from among the appliance positions with respect to a reference;
associating an anchor point with the maximum deviator;
setting an anchor point at a negative torque limit when the maximum deviator is above the reference; and
setting an anchor point at a positive torque limit when the maximum deviator is below the reference.

12. The method of claim 3, wherein computing a predicted final occlusion further comprises adjusting each orthodontic appliance based on the determined twist angles of the archwire.

13. The method of claim 12, wherein adjusting each orthodontic appliance comprises incrementally adjusting each orthodontic appliance based on the determined twist angles of the archwire until the twist angle of the archwire at each appliance position is within a defined tolerance of zero.

14. The method of claim 12, wherein adjusting each orthodontic appliance further comprises calculating an applied torque on each orthodontic appliance based on the determined twist angles of the archwire.

15. The method of claim 12, wherein adjusting each orthodontic appliance further comprises applying a resistance weight to each orthodontic appliance based on the associated tooth's relative resistance to movement.

16. The method of claim 15, wherein the resistance weight applied to each of the orthodontic appliances is based on at least one of overall root surface area of the associated tooth, root profile area of the associated tooth, root length in the associated tooth, and a number of roots in the associated tooth.

17. The method of claim 15, wherein the resistance weight applied to each of the orthodontic appliances is one of a scalar value or a vector value.

18. The method of claim 12, wherein adjusting each orthodontic appliance further comprises:
calculating a resultant torque value for each orthodontic appliance based on the determined twist angles of the archwire and a resistance weight corresponding to the associated tooth's relative resistance to movement; and
incrementally adjusting each orthodontic appliance based on the calculated resultant torque value.

19. The method of claim 1, wherein computing a predicted final occlusion comprises:
iteratively determining a twist angle of the archwire at each appliance position along the archwire; and
incrementally adjusting each tooth based on the determined twist angles until the twist angle at each appliance position along the archwire is within a defined tolerance of zero.

20. The method of claim 1, further comprising displaying a 3D representation of the computed final occlusion.

21. The method of claim 1, further comprising receiving data specifying the proposed orthodontic prescription from one of a practitioner or a database.

22. The method of claim 1, further comprising displaying an animated 3D representation of the dental arch from initial malocclusion to the predicted final occlusion.

23. The method of claim 1, further comprising displaying an animated 3D representation of the dental arch from an intended final occlusion to the predicted final occlusion.

24. The method of claim 1, wherein the orthodontic appliances comprise orthodontic appliances that couple with an archwire.

25. The method of claim 1, wherein the orthodontic appliances include at least one of brackets, buccal tubes, or sheaths.

26. The method of claim 3 wherein the twist angle of the archwire is defined as an angle between a labio-lingual vector of the archwire and a perpendicular projection of the labio-lingual vector onto a reference occlusal plane.

27. A system comprising:
a computing device;
modeling software executing on the computing device that provides digital representations of a proposed orthodontic prescription including a plurality of orthodontic appliances each associated with a different one of a plurality of teeth in a dental arch and an archwire received in a slot of each of the orthodontic appliances; and
a torque adjustment module that models archwire engagement with the appliances for the proposed orthodontic prescription within a three-dimensional (3D) modeling environment and computes a predicted final occlusion for the dental arch based on modeling the effects of torque loss experienced by digital representations of the archwire and the orthodontic appliances throughout a course of treatment with the proposed orthodontic prescription within the three-dimensional (3D) modeling environment.

28. The system of claim 27, further comprising a user interface to display the predicted final occlusion within the 3D environment.

29. The system of claim 27, wherein the torque adjustment module computes occlusions for the dental arch at discrete points in time throughout treatment with the proposed orthodontic prescription based on the modeled archwire engagement.

30. The system of claim 29, further comprising a user interface to display the computed occlusions at discrete points in time throughout treatment with the proposed orthodontic prescription within the 3D environment.

31. The system of claim 30, wherein the 3D representation of the computed occlusions at discrete points in time include at least one appliance and the archwire in a twisted geometric form.

32. The system of claim 30, wherein the 3D representation of the computed occlusions at discrete points in time includes an archwire rendered in varying color along the length of the archwire in correspondence with the torsional stress in each archwire segment.

33. The system of claim 32, wherein a color is varied by varying at least one of hue, saturation, brightness, chroma, lightness or shade as a function of torsional stress.

34. The system of claim 30, wherein appliances that engage the archwire are distinguished from appliances that do not engage the archwire by a difference in appearance.

35. The system of claim 34, wherein a difference in appearance includes a difference in at least one of hue, saturation, brightness, chroma, lightness, shade, opacity, transparency, or turbidity.

36. The system of claim 27, further comprising a user interface to display the modeled archwire engagement with the appliances within the 3D environment.

37. The system of claim 27, wherein torque loss includes at least one of incomplete archwire expression and less than full engagement of the archwire in the slots of each of the orthodontic appliances.

38. The system of claim 27, wherein the torque adjustment module determines a twist angle of the archwire at each appliance position along the archwire to model the archwire engagement with the appliances.

39. The system of claim 38, wherein the torque adjustment module iteratively determines the twist angle at each appliance position along the archwire.

40. The system of claim 38, wherein the torque adjustment module determines a torque angle for each orthodontic appliance, and determines positive and negative torque limits of the archwire for each orthodontic appliance.

41. The system of claim 40, wherein the torque adjustment module determines the torque angle for each orthodontic appliance with respect to a reference occlusal plane.

42. The system of claim 38, wherein the torque adjustment module:
    identifies anchor points for the archwire from among the appliance positions;
    generates line segments between anchor points; and
    determines the twist angle based on the line segment associated with each appliance position.

43. The system of claim 42, wherein torque adjustment module:
    defines a reference line;
    identifies a maximum deviator from among the appliance positions with respect to the reference line;
    sets the anchor point at a negative torque limit when the maximum deviator is above the current reference line; and
    sets the anchor point at a positive torque limit when the maximum deviator is below the current reference line.

44. The system of claim 38, wherein the torque adjustment module adjusts each orthodontic appliance based on the determined twist angles.

45. The system of claim 38, wherein the torque adjustment module incrementally adjusts each orthodontic appliance based on the determined twist angles until the twist angle at each appliance position along the archwire is within a predefined tolerance of zero.

46. The system of claim 38, wherein the torque adjustment module calculates an applied torque on each orthodontic appliance based on the determined twist angles.

47. The system of claim 38, wherein the torque adjustment module applies a resistance weight to each orthodontic appliance based on the associated tooth's relative resistance to movement.

48. The system of claim 47, wherein the resistance value applied to each of the orthodontic appliances is based on at least one of root surface area of the associated tooth and a number of roots of the associated tooth.

49. The system of claim 47, wherein the resistance value applied to each of the orthodontic appliances is one of a scalar value and a vector value.

50. The system of claim 48, wherein the torque adjustment module:
    calculates a resultant torque value for each orthodontic appliance based on the determined twist angles and a resistance weight corresponding the associated tooth's relative resistance to movement; and
    incrementally adjusts each orthodontic appliance based on the resultant torque value.

51. The system of claim 38 wherein the twist angle of the archwire is defined as an angle between a labio-lingual vector of the archwire and a perpendicular projection of the labio-lingual vector onto a reference occlusal plane.

52. The system of claim 27, wherein the torque adjustment module:
    iteratively determines a twist angle of the archwire at each appliance position along the archwire; and
    incrementally adjusts each tooth based on the determined twist angles until the twist angle at each appliance position along the archwire is within a defined tolerance of zero.

53. The system of claim 27, wherein the torque adjustment module receives data specifying the proposed orthodontic prescription from one of a practitioner or a database.

54. The system of claim 27, wherein the orthodontic appliances comprise orthodontic appliances that couple with an archwire.

55. The system of claim 27, wherein the orthodontic appliances include at least one of brackets, buccal tubes, or sheaths.

56. The system of claim 27, wherein the orthodontic appliances include at least one of brackets with tiewings or self ligating brackets.

57. A method comprising:
    digitally representing a proposed orthodontic prescription that includes a plurality of orthodontic appliances each associated with a different one of a plurality of teeth in a dental arch and an archwire received in a slot of each of the orthodontic appliances; and
    modeling engagement of the archwire with the orthodontic appliances based on twisting of the archwire within the slots of the orthodontic appliances to model effects of torque loss experienced by digital representations of the archwire and the orthodontic appliances throughout a course of treatment with the proposed orthodontic prescription within a three-dimensional (3D) environment.

58. The method of claim 57 wherein engagement of the archwire with each of the orthodontic appliances is modeled throughout a course of treatment with the proposed orthodontic prescription.

59. The method of claim 57 further comprising computing a predicted final occlusion for the dental arch based on the modeled engagement of the archwire with each of the orthodontic appliances throughout a course of treatment with the proposed orthodontic prescription.

60. The method of claim 57, wherein the archwire may twist within a slop zone associated with each orthodontic appliance, wherein the slop zone is an area between a positive torque limit and a negative torque limit of the archwire within the slot.

61. The method of claim 60 wherein the slop zones for each orthodontic appliance are independent of each other.

62. The method of claim 60, wherein the slop zone depends upon a torque angle of the appliance slot with respect to the reference occlusal plane and a size of the archwire.

63. The method of claim 57 further comprising adjusting each orthodontic appliance and a tooth associated with the orthodontic appliance based on the modeled archwire engagement.

64. The method of claim 57 wherein twisting of the archwire within the slots of the orthodontic appliances is defined as a twist angle between a labio-lingual vector of the archwire and a perpendicular projection of the labio-lingual vector onto a reference occlusal plane.

* * * * *

UNITED STATES PATENT AND TRADEMARK OFFICE
CERTIFICATE OF CORRECTION

Page 1 of 1

PATENT NO.         : 7,869,983 B2
APPLICATION NO.    : 10/990925
DATED              : January 11, 2011
INVENTOR(S)        : Richard E. Raby It is certified that error appears in the above-identified patent and that said Letters Patent is hereby corrected as shown below:

Sheet 5 of 20
Reference Numeral 124; Fig. 5, Line 1, delete "INTIAL" and insert -- INITIAL --, therefor.

Column 1
Line 32; delete "flat-reference" and insert -- flat reference --, therefor.

Column 28
Line 37; delete "form" and insert -- from --, therefor.

Column 32
Line 34-35; Claim 56, delete "self ligating" and insert -- self-ligating --, therefor.

Signed and Sealed this
Twenty-ninth Day of March, 2011

David J. Kappos
*Director of the United States Patent and Trademark Office*